:::: {.flex-container}
(12) United States Patent  
Hutkins et al.

(10) Patent No.: US 11,752,178 B2  
(45) Date of Patent: Sep. 12, 2023
::::

(54) METHODS FOR THE ISOLATION OF MICROBES WITH ENHANCED PERSISTANCE AND COMPOSITIONS WITH SUCH MICROBES

(71) Applicant: NUtech Ventures, Lincoln, NE (US)

(72) Inventors: Robert Hutkins, Lincoln, NE (US); Car Reen Kok, Lincoln, NE (US); Maria X. Maldonado-Gomez, Sacramento, CA (US)

(73) Assignee: NUtech Ventures, Lincoln, NE (US)

( * ) Notice: Subject to any disclaimer, the term of this patent is extended or adjusted under 35 U.S.C. 154(b) by 41 days.

(21) Appl. No.: 16/852,236

(22) Filed: Apr. 17, 2020

(65) Prior Publication Data

US 2021/0069266 A1   Mar. 11, 2021

Related U.S. Application Data

(60) Provisional application No. 63/000,915, filed on Mar. 27, 2020, provisional application No. 62/881,911, filed on Aug. 1, 2019, provisional application No. 62/835,279, filed on Apr. 17, 2019.

(51) Int. Cl.
| | |
|---|---|
| *A23L 33/135* | (2016.01) |
| *A61K 35/745* | (2015.01) |
| *A23L 33/21* | (2016.01) |
| *A61K 47/36* | (2006.01) |
| *A61K 9/19* | (2006.01) |

(52) U.S. Cl.
CPC .......... *A61K 35/745* (2013.01); *A23L 33/135* (2016.08); *A23L 33/21* (2016.08); *A61K 47/36* (2013.01); *A23Y 2300/55* (2013.01); *A23Y 2300/59* (2013.01); *A61K 9/19* (2013.01)

(58) Field of Classification Search
CPC .......... A23L 33/135; A23L 5/00; A23L 33/21; A61K 35/745; A61K 35/741; A61K 2300/00; A61K 31/702; A61K 47/36; A61K 9/19; A23Y 2300/55; A23Y 2300/59; A61P 1/00
See application file for complete search history.

(56) References Cited

U.S. PATENT DOCUMENTS

| | | | |
|---|---|---|---|
| 9,629,908 B2* | 4/2017 | Benyacoub | A61P 33/02 |
| 2012/0034200 A1 | 2/2012 | Porubcan | |
| 2012/0207712 A1 | 8/2012 | Longini et al. | |
| 2013/0095204 A1* | 4/2013 | Jouni | A23P 10/35 |
| | | | 426/74 |
| 2017/0058270 A1* | 3/2017 | Garcia-Garcia | A23C 9/1203 |
| 2017/0106029 A1* | 4/2017 | Ranganathan | A61K 9/48 |
| 2017/0165302 A1 | 6/2017 | Henn et al. | |
| 2017/0368110 A1 | 12/2017 | Grant et al. | |
| 2018/0016647 A1 | 1/2018 | Van Sinderen et al. | |
| 2018/0153951 A1* | 6/2018 | Zhong | A61K 45/06 |
| 2019/0307802 A1* | 10/2019 | Vollmer | A23K 10/16 |

FOREIGN PATENT DOCUMENTS

| | | | | |
|---|---|---|---|---|
| CN | 111280252 A | * | 6/2020 | .......... A23C 9/1234 |
| WO | 2017156550 A1 | | 9/2017 | |

OTHER PUBLICATIONS

Kondepudi et al., Prebiotic-non-digestible oligosaccharides preference of probiotic bifidobacteria and antimicrobial activity against Clostridium difficile, Anaerobe, vol. 18, p. 489-497. (Year: 2012).*
Maldonado-Gomez et al., Stable Engraftment of Bifidobacterium longum AH1206 in the Human Gut Depends on Individualized Features of the Resident Microbiome, Cell Host & Microbe, p. 515-526, vol. 20. (Year: 2016).*
Result 2 sequence search result Bifidobacterium longum sbsp. longum AH1206 (Year: 2022).*

* cited by examiner

*Primary Examiner* — Taeyoon Kim
*Assistant Examiner* — Tiffany M Gough
(74) *Attorney, Agent, or Firm* — Tracey S. Truitt; Sandberg Phoenix & von Gontard P.C.

(57) ABSTRACT

Particularly effective prebiotic-probiotic combinations including a novel probiotic, *B. longum* subsp *longum*, and XOS and *B. pseudocatenulatum* with Xylo-oligosaccharides are provided, together with methods of identifying synergistic probiotic-prebiotic combinations. Additionally, kits comprising the probiotic(s) and prebiotic(s) are also provided.

17 Claims, 15 Drawing Sheets

Specification includes a Sequence Listing.

FIG. 3 (CONT.)
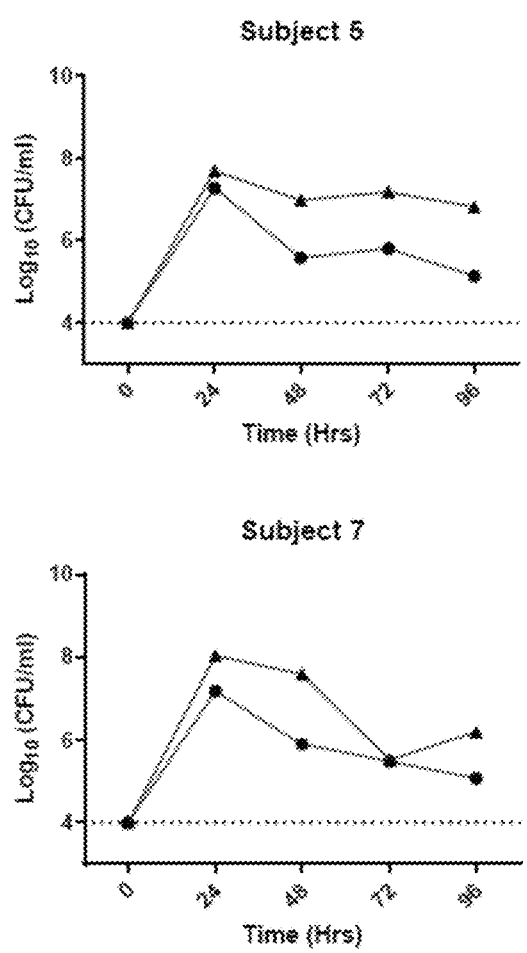
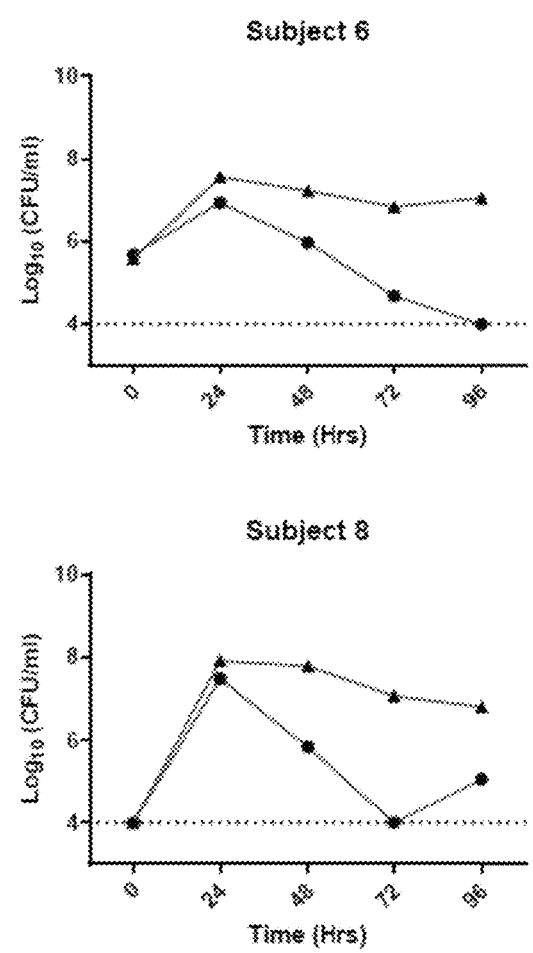

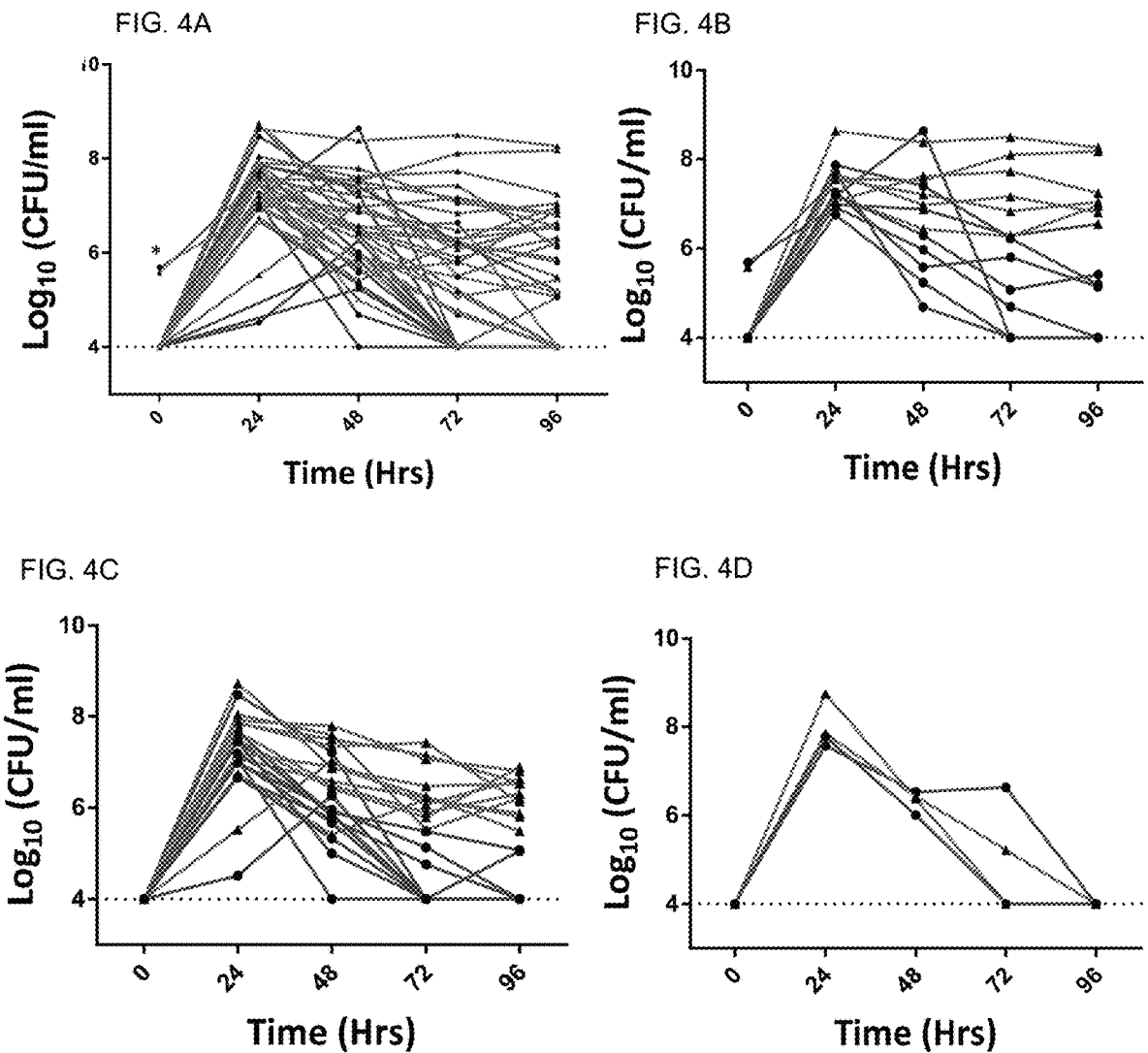

FIG. 7A
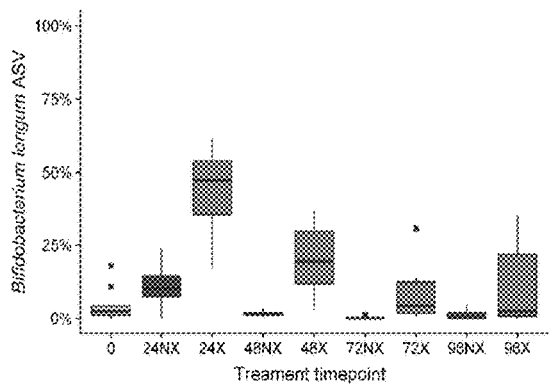
FIG. 7B
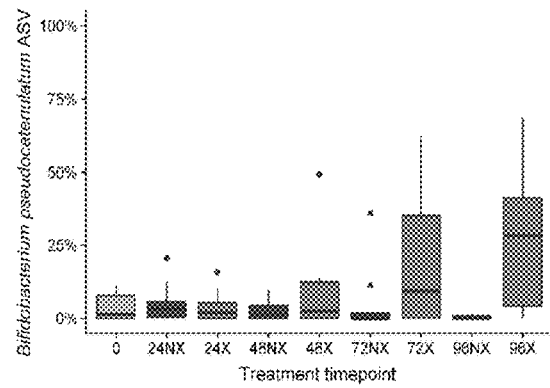
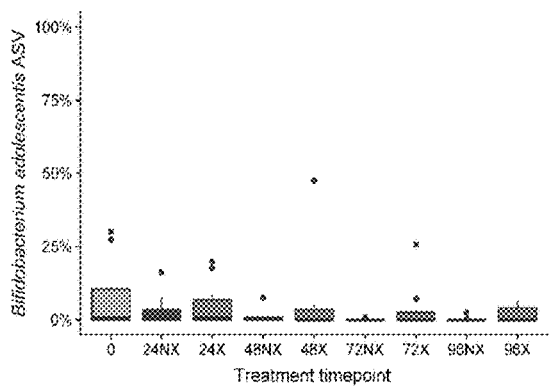
FIG. 7C
FIG. 8A
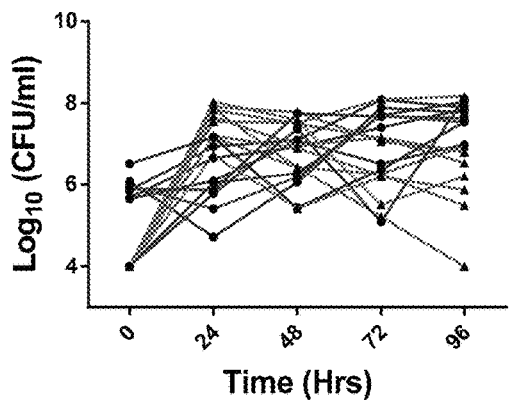
FIG. 8B
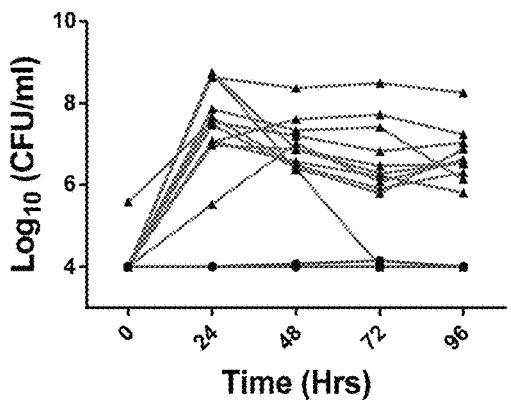

METHODS FOR THE ISOLATION OF MICROBES WITH ENHANCED PERSISTANCE AND COMPOSITIONS WITH SUCH MICROBES

SEQUENCE LISTING

This application contains a sequence listing in paper format and in computer readable format, the teachings and content of which are hereby incorporated by reference.

BACKGROUND OF THE DISCLOSURE

It is now well accepted that the composition and function of the gastrointestinal microbiome plays a major role in maintaining host health. How the human gut microbiome is affected by diet is one of the most important areas of research in the food, nutrition, and biomedical sciences. In particular, a disrupted or dysbiotic microbiota has been suggested to contribute to a wide range of gastrointestinal and systemic diseases. Researchers are now especially interested in developing therapeutic or dietary approaches to correct or redress these imbalances.

A frequent outcome of many biomedical reports and clinical trials is the observation that a particular treatment may be effective in some individuals, but not in others. This responder/non-responder phenomenon is also common in trials using probiotics, prebiotics, and other gut health interventions. For example, while prebiotic supplementations have been shown in numerous clinical studies to induce a bifidogenic response, there are often study participants for whom this expected response does not occur. Identifying or predicting responders and non-responders based on their resident microbiota remains a significant challenge.

Several explanations may account for the non-responder phenotype. For prebiotics, non-responders may lack the relevant strains that are physiologically or biochemically equipped to utilize that particular substrate. Alternatively, even if such strains were present, other members of the microbiota may simply out-compete those strains for the substrate. Similarly, probiotics are also subject to host-specific effects. To reach the colon, it is possible that ingested strains may not survive digestion through the stomach and small intestine. In the colon, they may be inhibited or outcompeted by other gut commensals.

One approach to enrich for beneficial microbes in the gut is to introduce specific strains in the form of synbiotics. Ideally, these synbiotics would be comprised of prebiotic-probiotic combinations, such that the prebiotic is specifically and preferentially fermented by the probiotic. The rational for this approach is based on classic ecological theory. Specifically, Tilman's resource ratio competition model states that the dominance of certain taxa is dependent upon the availability and demand for particular resources along with the rate of nutrient consumption. Thus, if the synbiotic was formulated such that the prebiotic specifically stimulated the growth of the companion probiotic, the latter would have a greater opportunity to become established in the gut. Indeed, previous studies described the possible persistence of probiotics when administered as a synbiotic.

Synbiotics that are appropriately designed also have the potential to increase the responder rate, by converting non-responders into responders. These so-called synergistic synbiotics were envisioned more than a decade ago, but few successful formulations of synergistic synbiotics have been reported. This is most likely due to the lack of strategic methods for pairing prebiotics and probiotics that can demonstrate synergism.

Recently, we described one such approach called in vivo selection or IVS. Briefly, an autochthonous strain (i.e., a normal resident of the gastrointestinal tract) of *Bifidobacterium adolescentis* was enriched in vivo by the prebiotic, galactooligosaccharide (GOS), and then recovered by cultural methods. When the enriched strain (*B. adolescentis* IVS-1) was recombined with GOS as a synbiotic and introduced to rodents, abundance of IVS-1 increased to 37%. The enhanced abundance of the IVS-1 strain was considered to be due to the ability of this strain to consume GOS more rapidly than its competitors, including other resident bifidobacteria. Although abundance of IVS-1 was not increased when combined with the prebiotic in humans subjects, the strain still reached higher levels of abundance compared to an allochthonous strain (i.e., a non-resident of the gastrointestinal tract) of *Bifidobacterium* (Krumbeck et al., 2018).

Despite the potential of the IVS approach for isolating autochthonous synergistic strains with putative beneficial properties, this method requires, at minimum, that a human subject study be conducted. In contrast, if a reproducible in vitro strategy could be devised to mimic the IVS method, it would be possible to obtain similar strains in a faster and more cost-effective manner.

This disclosure proposes the concept of in vitro enrichment (IVE) as an alternative strategy to select for potentially synergistic putative probiotic strains. Autochthonous strains of *Bifidobacterium* were enriched through a step-wise batch fecal fermentation model using a targeted approach. Such strains obtained by IVE would be expected to be competitive in the gut environment when combined with the cognate prebiotic. In this study we used the prebiotic xylooligosaccharide (XOS) and successfully obtained a *Bifidobacterium* strain that demonstrated synergism when reintroduced with XOS into in vitro fecal environments from multiple donors.

BRIEF DESCRIPTION OF THE DISCLOSURE

In one aspect of the disclosure, a synergistic combination of a probiotic species and a prebiotic (a "complementary synbiotic" or "synbiotic") is provided. In some forms, the probiotic species is selected from the group consisting of *B. pseudocatenulatum, B. longum*, and any combination or extract thereof. In some forms, the prebiotic is xylooligosaccharide (XOS). In some forms, the prebiotic is *B. longum* subsp *longum* CR15 or *B. pseudocatenulatum* CR16, preferably *B. longum* subsp *longum* CR15. In some forms, the prebiotic includes enzymes that assist with prebiotic utilization. In some forms, the enzymes include at least one member of the glycosyl hydrolase family. In some forms, the enzymes preferentially utilize XOS. In some forms, the enzymes include at least two different glycosyl hydrolase family members. In some forms, the *B. longum* subsp *longum* CR15 or *B. pseudocatenulatum* CR16 has a nucleotide sequence having at least 80%, 85, 90, 91, 92, 93, 94, 95, 96, 97, 98, 99, or 100% sequence identity to SEQ ID NO. 5 or SEQ ID NO. 6, respectively. CR15 can also be referred to as NCBI submission #PRJNA540282. In some forms, the *B. longum* or *B. pseudocatenulatum* have a contiguous nucleotide sequence that includes at least 1000, 950, 900, 850, 800, 750, 700, 650, 600, 550, 500, 450, 400, 350, 300, 250, 225, 200, 175, 150, 140, 130, 120, 110, 105, 100, 95, 90, 85, 80, 75, 70, 65, 60, 55, 50, 45, 40, 35, 30, 25, 24, 23, 22, 21, 20, 19, or 18 contiguous nucleotides having at least 90, 91, 92, 93, 94, 95, 96, 97, 98, 99, 99.1, 99.2, 99.3, 99.4, 99.5, 99.6, 99.7, 99.8, 99.9, or 100% sequence identity with a contiguous nucleotide sequence from SEQ ID NOs 5 or 6. Preferably, the contiguous nucleotide sequence from SEQ ID NO. 5 or 6 and the contiguous nucleotide sequence from *B. longum* or *B. pseudocatenulatum* are from the same genomic region. In some forms, the contiguous nucleotide sequence is selected from the group consisting of SEQ ID. NOs. 15-99 and any combination thereof. In some forms, the classification of a bacterial species as being *B. longum* or *B. pseudocatenulatum* is done by 16S sequencing. In some forms, the 16S sequencing will have at least 95, 96, 97, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9, or 100% sequence homology with the 16S sequence of *B. longum* subsp. *longum* or the 16S sequence of *B. pseudocatenulatum*. In some forms, the 16S sequence of *B. longum* subsp *longum* can be or corresponds to the sequence generated by the primer pair of SEQ ID NO. 3 and 4. In some forms, the 16S sequence of *B. pseudocatenulatum* can be or corresponds to the sequence generated by the primer pair of SEQ ID NO. 9 and 10. In some forms, the 16S sequence of *B. longum* subsp. *longum* will have at least 95, 96, 97, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9, or 100% sequence homology with SEQ ID NO. 13. In some forms, the 16S sequence of *B. pseudocatenulatum* will have at least 95, 96, 97, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9, or 100% sequence homology with SEQ ID NO. 14. In some forms, the prebiotic and probiotic are administered within 6 hours, more preferably 5 hours, still more preferably 4 hours, even more preferably 3 hours, still more preferably 2 hours, even more preferably 1 hour, still more preferably 45 minutes, even more preferably 30 minutes, still more preferably 15 minutes, even more preferably 5, 4, 3, 2, 1 minutes, and most preferably at the same time, of one another. In some forms, the probiotic and prebiotic are administered in a weight ratio range between about 100:1 to 1:100. In some forms, the probiotic and prebiotic are combined in a composition. In some forms, the composition is in a form selected from the group consisting of a liquid, gelatin, capsule, sachet, straws, tablet, powder, or combined with or introduced into a food product, or kit comprising both an amount of probiotic and an amount of prebiotic, together with instructions on administration or consumption. In some forms, the probiotic and prebiotic are in different forms, together with instructions for administration or consumption. In some forms, the probiotic and prebiotic are each administered 1, 2, 3, 4, 5, 6, 7, 8, 9, 10, or more times. In some forms, the prebiotic is administered 1, 2, 3, 4, 5, 6, 7, 8, 9, 10, or more times after the initial administration of the probiotic. In some forms, the probiotic is administered 1, 2, 3, 4, 5, 6, 7, 8, 9, 10, or more times after the initial administration of the prebiotic. In some forms, the probiotic and/or the prebiotic are administered orally, via a suppository, or via a microbiome transplant. In some forms, the amount of probiotic comprises between about $10^6$ to about $10^{12}$ CFU, more preferably $10^8$ to $10^{11}$ CFU, and most preferably about $10^9$-$10^{10}$ CFU per administration. In some forms, the probiotic and prebiotic are administered to an animal, preferably a mammal or poultry, and especially including humans, pigs, cows, dogs, cats, goats, sheep, turkeys, and chicken.

In another aspect of the disclosure, a method of determining a synergistic combination of probiotic and prebiotic is provided. In some forms, the method includes the steps of fermenting fecal matter, preferably in a slurry, with a prebiotic; transferring the fermenting fecal matter-prebiotic mixture into fresh medium at least once, and determining which probiotic strains were established and/or maintained. In preferred forms, there are a plurality of different fecal matter-prebiotic mixtures, each of which has a different prebiotic so that a comparison can be made as to which probiotics worked best or were the most successful at becoming established or maintained. In some forms, the fecal matter-prebiotic mixture is transferred to fresh medium at least 5, 10, 15, 16, 17, 18, 19, 20, 21, 22, 23, 24, 25, 26, 27, 28, 29, 30 times or more. In some forms, the determination of which probiotic strains were established and/or maintained includes the steps of plating samples of the fecal matter-prebiotic mixture onto a growth medium such as agar, more preferably an agar designed for growth of probiotics, and then identifying the probiotic strains through sequencing, such as 16S rRNA sequencing. In some forms, the fecal matter is supplemented with particular probiotic strains in order to compare the growth rates of the supplemented probiotic with the naturally occurring bacterial flora in the fecal matter. In some forms, the fecal matter is supplemented with 1, 2, 3, 4, 5, 6, 7, 8, 9, 10, or more probiotic strains. In some forms, the probiotic strains include *B. pseudocatenulatum*, *B. longum*, and any extract or combination thereof and in any form described above. In some forms, the prebiotic is XOS.

In another aspect of the disclosure, a method of modulating gastrointestinal microbiota of a subject is provided. Generally, the method comprises the step of administering a synergistic combination of at least one probiotic species and at least one prebiotic. In some forms, the probiotic species is selected from the group consisting of *B. pseudocatenulatum*, and *B. longum* and any combination or extract thereof, or in any form described above. In some forms, the prebiotic is xylooligosaccharide (XOS). In some forms, the prebiotic is *B. longum* subsp *longum* CR15 or *B. pseudocatenulatum* CR16, preferably *B. longum* subsp *longum* CR15. In some forms, the prebiotic and probiotic are administered within 6 hours, more preferably 5 hours, still more preferably 4 hours, even more preferably 3 hours, still more preferably 2 hours, even more preferably 1 hour, still more preferably 45 minutes, even more preferably 30 minutes, still more preferably 15 minutes, even more preferably 5, 4, 3, 2, 1 minutes, and most preferably at the same time, of one another. In some forms, the probiotic and prebiotic are administered in a weight ratio range between about 100:1 to 1:100. In some forms, the probiotic and prebiotic are combined in a composition. In some forms, the composition is in a form selected from the group consisting of a liquid, gelatin, capsule, tablet, powder, or kit comprising both an amount of probiotic and an amount of prebiotic, together with instructions on administration or consumption. In some forms, the probiotic and prebiotic are in different forms, together with instructions for administration or consumption. In some forms, the probiotic and prebiotic are each administered 1, 2, 3, 4, 5, 6, 7, 8, 9, 10, or more times. In some forms, the prebiotic is administered 1, 2, 3, 4, 5, 6, 7, 8, 9, 10, or more times after the initial administration of the probiotic and/or prebiotic. In some forms, the probiotic is administered 1, 2, 3, 4, 5, 6, 7, 8, 9, 10, or more times after the initial administration of the prebiotic and/or probiotic. In some forms, the probiotic and/or the prebiotic are administered orally, via a suppository, or via a microbiome transplant. In some forms, the amount of probiotic comprises between about $10^6$ to about $10^{12}$ CFU, more preferably $10^8$ to $10^{11}$ CFU, and most preferably about $10^9$-$10^{10}$ CFU per administration. In some forms, the probiotic and prebiotic are administered to an animal, preferably a mammal or poultry, and especially including humans, pigs, cows, dogs, cats, goats, turkeys, chickens, and sheep.

In another aspect of the disclosure, a method of improving gut and/or systemic health is provided. In some forms, the improved gut and/or systemic health can be determined by assessing a gastrointestinal characteristic or parameter. In some forms, the improved gut and/or systemic health is determined through at least one of improved laxation and regularity, improved satiety, improved gut barrier function, less bloating and gas, reduced risk of gastrointestinal infections, reduced duration of colic symptoms, and/or reduced risk of atopic dermatitis. In some forms, the improvement is in comparison to a subject or group of subjects that has not had an administration of a probiotic and/or prebiotic, as described above. In some forms, the improvement is in comparison to the same subject before and after administration of a composition in accordance with the present disclosure. In some forms, the improvement is at least 10, 20, 30, 40, 50, 60, 70, 80, 90%, or more. Generally, the method comprises the step of administering a synergistic combination of at least one probiotic species and at least one prebiotic. In some forms, the probiotic species is selected from the group consisting of *B. pseudocatenulatum*, and *B. longum* and any combination or extract thereof. In some forms, the prebiotic is xylooligosaccharide (XOS). In some forms, the prebiotic is *B. longum* subsp *longum* CR15 or *B. pseudocatenulatum* CR16, preferably *B. longum* subsp *longum* CR15, or in any form described above. In some forms, the prebiotic and probiotic are administered within 6 hours, more preferably 5 hours, still more preferably 4 hours, even more preferably 3 hours, still more preferably 2 hours, even more preferably 1 hour, still more preferably 45 minutes, even more preferably 30 minutes, still more preferably 15 minutes, even more preferably 5, 4, 3, 2, 1 minutes, and most preferably at the same time, of one another. In some forms, the probiotic and prebiotic are administered in a weight ratio range between about 100:1 to 1:100. In some forms, the probiotic and prebiotic are combined in a composition. In some forms, the composition is in a form selected from the group consisting of a liquid, gelatin, capsule, tablet, powder, or kit comprising both an amount of probiotic and an amount of prebiotic, together with instructions on administration or consumption. In some forms, the probiotic and prebiotic are in different forms, together with instructions for administration or consumption. In some forms, the probiotic and prebiotic are each administered 1, 2, 3, 4, 5, 6, 7, 8, 9, 10, or more times. In some forms, the prebiotic is administered 1, 2, 3, 4, 5, 6, 7, 8, 9, 10, or more times after the initial administration of the probiotic and/or prebiotic. In some forms, the probiotic is administered 1, 2, 3, 4, 5, 6, 7, 8, 9, 10, or more times after the initial administration of the prebiotic and/or probiotic. In some forms, the probiotic and/or the prebiotic are administered orally or via a microbiome transplant. In some forms, the amount of probiotic comprises between about $10^6$ to about $10^{12}$ CFU, more preferably $10^8$ to $10^{11}$ CFU, and most preferably about $10^9$-$10^{10}$ CFU per administration. In some forms, the probiotic and prebiotic are administered to an animal, preferably a mammal or poultry, and especially including humans, pigs, cows, dogs, cats, goats, turkeys, chickens, and sheep.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 4A is a graph illustrating a summary of the establishment trends of *B. longum* subsp. *longum* CR15 in all 20 samples in the presence (▲) or absence (•) of XOS and showing that *B. longum* subsp. *longum* CR15 was clearly established in 7 samples. Time 0 samples were taken prior to inoculation of $10^7$ CFU/mL of the test strains. Horizontal dashed lines indicate the limits of detection ($10^4$ CFU/mL);

FIG. 4B is a graph illustrating that *B. longum* subsp. *longum* CR15 was potentially established in 11 samples. Time 0 samples were taken prior to inoculation of $10^7$ CFU/mL of the test strains. Horizontal dashed lines indicate the limits of detection ($10^4$ CFU/mL);

FIG. 4C is a graph illustrating that *B. longum* subsp. *longum* CR15 was displaced or washed out in 2 samples. Time 0 samples were taken prior to inoculation of $10^7$ CFU/mL of the test strains. Horizontal dashed lines indicate the limits of detection ($10^4$ CFU/mL);

FIG. 4D is a graph illustrating that in the absence of XOS, the *B. longum* subsp. *longum* CR15 strain could not be established in any of the samples. Varying trends of establishment of *B. longum* subsp. *longum* CR15 were observed across fecal samples. Time 0 samples were taken prior to inoculation of $10^7$ CFU/mL of the test strains. Horizontal dashed lines indicate the limits of detection ($10^4$ CFU/mL);

FIG. 7A is a graph illustrating an abundance of ASVs corresponding to *B. longum* in the presence of XOS displayed as relative abundance at each time point. 0; baseline of samples at the start of fermentation; NX, fermentation without XOS; X, fermentations with XOS;

FIG. 7B is a graph illustrating an abundance of ASV's corresponding to *B. pseudocatenulatum* in the presence of XOS displayed as relative abundance at each time point. 0; baseline of samples at the start of fermentation; NX, fermentation without XOS; X, fermentations with XOS:

FIG. 7C is a graph illustrating an abundance of *B. adolescentis* in the presence of XOS displayed as relative abundance at each time point. 0; baseline of samples at the start of fermentation; NX, fermentation without XOS; X, fermentations with XOS;

FIG. 8A is a graph illustrating the enrichment of *B. longum* subsp. *longum* CR15 (▲) in the presence of XOS;

FIG. 8B is a graph illustrating the enrichment of *B. pseudocatenulatum* (•) in the presence of IOS. When present at baseline (9 samples), *B. pseudocatenulatum* reached high cell numbers at the end of fermentation (A). When *B. pseudocatenulatum* was below detection at baseline (11 samples), the species remained undetected after 96 hours;

DETAILED DESCRIPTION

Figure 1A:
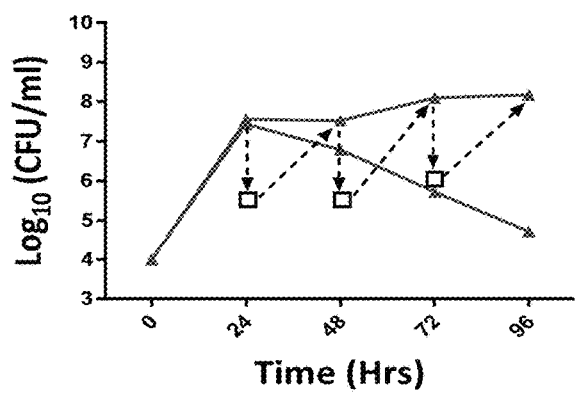
FIG. 1A is a graph illustrating hypothetical trends of successful (green) and unsuccessful enrichments (red) in fermentation experiments of bifidobacteria enriched by XOS in fecal environments whereas strain establishment was dependent on the strain and the host.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In some forms, the methods of the present disclosure are directed to administering at least one probiotic, preferably selected from the group consisting of *B. pseudocatenulatum*, *B. longum*, and any extract or combination, to a subject, and preferably to a subject in need thereof. As used herein, "subject in need thereof" refers to a subset of subjects in need of improving their gastrointestinal microbiota and/or their gut health and/or their systemic health. In one embodiment, subjects that are in need thereof may include animals, mammals, poultry, and more preferably humans, pigs, cows, dogs, cats, goats, turkey, chicken, and sheep. Additionally, the methods include administering a prebiotic, preferably a prebiotic that works synergistically with the administered probiotic, or the bacterial strain or strains that are in need of establishment and proliferation within the gut microbiota. In some preferred forms, the probiotic is *B. longum* subsp *longum*.

The term "administering" as used herein includes all means of introducing the bacterial strains and/or their extracts as well as the prebiotics described herein to the subject, including, but not limited to, oral (po), inhalation, buccal, sublingual, via suppository, microbiome transplantation, and the like. The strains and/or extracts as well as the prebiotics described herein may be administered in unit dosage forms and/or formulations containing conventional nontoxic pharmaceutically-acceptable carriers, adjuvants, and vehicles. The probiotic and/or extract thereof and the prebiotic do not need to be administered in the same way or in the same form.

Illustrative formats for oral administration include liquids, solids, tablets, pills, capsules, solids in a liquid medium, powders, lozenges, straws, sachets, cachets, solutions, elixirs, suspensions, emulsions, solutions, syrups, aerosols, soft and hard gelatin capsules, sterile packaged powders, or combined with or introduced into a food product.

In particularly suitable embodiments, the methods of the present disclosure include incorporating the probiotic(s) or extracts thereof and prebiotic(s) into the diet of the subject. In some forms, the probiotics can include live cultures or lyophilized preparations.

In some embodiments, a therapeutically effective amount of the probiotic(s) or extracts thereof in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, for example, *B. pseudocatenulatum, B. longum*, and any extract or combination thereof can be administered in the form of liquids, solids, tablets, pills, capsules, solids in a liquid medium, powders, lozenges, straws, sachets, cachets, solutions, elixirs, suspensions, emulsions, solutions, syrups, aerosols (as a solid or in a liquid medium), soft and hard gelatin capsules, sterile packaged powders, or combined with or introduced into a food product.

The term "therapeutically effective amount" as used herein, refers to that amount of active compound or agent that elicits the biological or medicinal response in a tissue system, animal or human that is being sought by a researcher, veterinarian, medical doctor or other clinician, which includes alleviation of the symptoms of the disease, condition or ailment being treated. In one aspect, the therapeutically effective amount is that which may treat or alleviate the condition, disease or symptoms of the disease at a reasonable benefit/risk ratio applicable to any medical treatment. The specific therapeutically-effective dose level for any particular patient will depend upon a variety of factors, including the severity of the condition being treated; the specific composition employed; the age, body weight, general health, gender and diet of the patient: the time of administration, route of administration, and the duration of the treatment; drugs used in combination or coincidentally with the probiotic(s) or extracts thereof and prebiotic(s); and like factors well known to the medical doctor, researcher, veterinarian, or other clinician of ordinary skill.

It is also appreciated that the therapeutically effective amount is advantageously selected with reference to any toxicity, or other undesirable side effect, that might occur during administration of the probiotic(s) such as *B. pseudocatenulatum, B. longum*, and any extract or combination thereof.

"Prebiotic" as used herein, refers to a substrate that exerts health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Some combinations of probiotic(s) such as *B. pseudocatenulatum, B. longum*, and any extract or combination thereof and/or at least one prebiotic, such as XOS, will act synergistically with one another. Such prebiotics may be naturally-occurring, synthetic, or developed through the genetic manipulation of organisms and/or plants, whether such new source is now known or developed later. Prebiotics useful in the present disclosure may include soluble starch, yeast extract, oligosaccharides, polysaccharides, and other prebiotics that contain fructose, xylose, soya, galactose, glucose and mannose. XOS is particularly preferred for some forms.

More specifically, prebiotics useful in the present disclosure may include soluble starch, yeast extract, polydextrose, polydextrose powder, lactulose, lactosucrose, raffinose, gluco-oligosaccharide, inulin, fructo-oligosaccharide, iso-malto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

In an embodiment, the total amount of prebiotics present in the composition may be from about 1.0 g/L to about 30.0 g/L including 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal.

The prebiotics of this disclosure can be in the same capsule or formulation as the probiotics, or in a separate dosage form. In some forms, the prebiotic and probiotic are in contact with one another in the composition. The prebiotics and compositions of this disclosure may also be taken with carbohydrate or fiber to increase their effectiveness.

The compositions of the present disclosure can also include one or more additional active ingredients, excipients, dissolution agents, surfactants, antioxidants, antiseptics, preservatives, penetrants, osmoprotectants, cryoprotectants, and combinations thereof.

Various excipients can be mixed with the compositions as would be known to those skilled in the art. Suitable excipients include, for example, microcrystalline cellulose, maltodextrin, colloidal silicon dioxide, lactose, starch, sorbitol, cyclodextrin and combinations thereof.

Suitable dissolution agents include, for example, organic acids such as citric acid, fumaric acid, lactic acid, tartaric acid, succinic acid, ascorbic acid, acetic acid, malic acid, glutaric acid and adipic acid, and can be used alone or in combination. These agents can also be combined with salts of the acids, e.g. sodium citrate with citric acid, to produce a buffer system.

Suitable surfactants include, for example, sodium lauryl sulphate, polyethylene separates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters.

Suitable antioxidants include, for example, sodium metabisulfite, tocopherols such as α, β, δ-tocopherol esters and α-tocopherol acetate, ascorbic acid and pharmaceutically acceptable salts thereof, ascorbyl palmitate, alkyl gallates (e.g., propyl gallate, TENOX® PG, TENOX® S-1), sulfites and pharmaceutically acceptable salts thereof, butylated hydroxyanisole, butylated hydroxytoluene, and monothioglycerol.

Suitable antiseptics include, for example, chlorhexidine gluconate, glucono delta-lactone, methylparaben, sodium hydroxide, and combinations thereof.

Suitable preservatives include parabens. Suitable parabens include, for example, methylparaben (E number E218), ethylparaben (E214), propylparaben (E216), butylparaben and heptylparaben (E209). Less common, but still suitable parabens include isobutylparaben, isopropylparaben, benzylparaben and their sodium salts.

Suitable penetrants include, for example, sulphoxides (e.g., dimethyl sulphoxide, dimethylacetamide, dimethylformamide), azone (1-dodecylazacycloheptan-2-one or laurocapran), pyrrolidones (e.g., N-methyl pyrolidone), fatty acids (e.g., oleic acid, lauric acid, myristic acid, capric acid), essential oils (e.g., *eucalyptus, chenopodium*, ylang-ylang, L-menthol), terpenes (e.g., sesquiterpene), terpenoids, oxazolidinones (e.g., 4-decyloxazolidin-2-one), and urea.

When producing a lyophilized form of a probiotic for use with the present disclosure, the probiotic strains are centrifuged at 3000×g for 15 minutes at room temperature and the resulting cell pellet is suspended in 10 ml of 20% glycerol in spent media resuspension solution (the media collected after centrifugation is mixed with 50% sterile glycerol to generate a 20% resuspension solution). The resulting cell suspension is snap frozen in liquid nitrogen and is then freeze dried to obtain a freeze dried viable cell product. 10 milligrams of the freeze dried cells is suspended in peptone water and is spread on brain heart infusion agar plates to determine viable colony forming units (CFUs) per milligram of freeze dried product. Alternatively, lyophilization can be scaled up in an appropriate industrial or commercial manufacturing processes wherein cells are harvested from high-cell density fermentors by continuous centrifugation and the slurries are frozen and lyophilized.

The following examples further illustrate specific embodiments of the present disclosure; however, the following illustrative examples should not be interpreted in any way to limit the disclosure.

EXAMPLES

Example 1

In this Example, stepwise in vitro fermentations to enrich for strains able to use XOS were performed and the most successful strains were identified and characterized.

Methods

Sample Collection

A total of 20 fecal samples were collected from volunteers throughout the duration of the study. Each participant was asked to sign a consent form indicating no known gastrointestinal disease, was 19 years of age or older, had not consumed antibiotics or probiotic supplements in the last 6 months, was not a regular consumer of yogurt, and was willing to provide 1 to 3 stool samples over three months. Participants were given a commode specimen collection kit (Fisher Scientific, New Hampshire, USA) and detailed instructions for collection and preservation. The study was approved by the UNL Institutional Review Board (IRB 20160616139).

Samples were collected and processed in an anaerobic chamber (Bactron IV Anaerobic Chamber, Sheldon Manufacturing, Cornelius, OR USA, 5% $H_2$, 5% $CO_2$, 90% $N_2$). Samples were diluted (1:10) in phosphate-buffered saline (PBS) at pH 7, homogenized, and stored in 2 ml aliquots at −80° C.

Step-Wise Fecal Fermentations

For all enrichment and establishment experiments XOS95™, a 95% pure prebiotic substrate with a degree of polymerization ranging from DP 2 to DP 20 was used (Prenexus Health, Arizona, US). For all fermentations, each fecal sample was treated as an individual experimental unit. In enrichment experiments, step-wise in vitro batch fermentations were performed. Diluted fecal slurries were homogenized, filtered and mixed with fermentation broth in a 6:3 ratio (v/v) in a total volume of 9.0 ml. When added, XOS was present at a concentration of 1%. All fermentations were incubated anaerobically at 37° C. After 24 hours, 100-fold dilutions were performed by transferring 100 ul of sample into 9.9 ml of fermentation broth containing XOS. Three subsequent transfers were performed every 24 hours, for a total of 96 hours. Samples at 0, 24, 48, 72, and 96 hours were collected and stored at −20° C. for DNA extraction and SCFA analysis. At the end of the four fermentation cycles (96 hours), samples were plated onto *Bifidobacterium* Selective Iodoacetate Mupirocin (BSIM) and colonies were picked. Each colony isolated was grown in modified de Man, Rogosa and Sharpe (mMRS) to which glucose was omitted, but supplemented with 1% XOS (mMRS-XOS) The isolates were stored at −20° C. for subsequent DNA extraction and 16S Sanger sequencing and identification.

For the establishment experiments, similar batch-wise fermentations were conducted, except that the XOS-enriched strains obtained from above were inoculated at the beginning of the fermentation cycle. Test strains were first incubated in MRS broth for 24 hours and used to inoculate (1%) fresh fecal fermentation media, with or without 1% XOS. Subsequent transfers were carried out as before. Samples were collected every 24 hours for up to 7 days, and isolates were picked from BISM plates, grown in mMRS-XOS and stored. Initial enrichment experiments were performed with 3 fecal samples, and 20 samples were used for subsequent establishment experiments with *B. longum* subsp. *longum* CR15.

DNA Extraction and 16S Sanger Sequencing and Analysis

DNA from the samples collected (fermentation media and isolates) were extracted using phenol-chloroform as described by Martinez et al. (2015), except that incubation times were for 30 minutes and DNA pellets were resuspended in 100 µl of DNase-free water. For the isolates, PCR was performed using 16S primers; 8F (5'-AGAGTTTGATCCTGGCTCAG-3') (SEQ ID NO. 1) and 1391R (5'-GACGGGCGGTGTGTRCA-3') (SEE ID NO 2) and PCR products were purified using QIAquick PCR Purification Kit (Qiagen, Hilden, Germany) and quantified with a NanoDrop ND-1000 Spectrophotometer (Thermo Fisher, Massachusetts, USA). The purified PCR products were sequenced by the Genomics Core Facility at Michigan State University.

Preliminary identification of potential IVE probiotic isolates was done using NCBI BLASTn. Isolates were assigned genus and species based on this blast search and were considered unique strains if isolated from different individuals.

Quantification of Bifidobacteria Using qRT-PCR

For all in vitro fermentation experiments, quantification of bacterial groups in the fermentation samples was performed by quantitative PCR (qPCR) using a Mastercycler Realplex2 (Eppendorf AG, Hamburg, Germany). Each reaction mixture contained 12.5 µl of qPCR Master Mix (2× Maxima SYBR green; Thermo Fisher Scientific, Massachusetts, USA), 0.4 µM of specific primers for each target organism, 8.5 µl of water, and 3 µl of template DNA for a final volume of 25 µl. Duplicate wells were used for each sample. Samples that had a standard deviation greater than 0.5 were re-analysed. For each assay, standard curves were made using DNA isolated from pure cultures from which counts were determined through plate counting. A 10-fold serial dilution of the DNA standards were made and the cycle threshold (ct) values of the standards were plotted against $log_{10}$ CFU/ml values. The *Bifidobacterium* genomes used for *B. longum* CR15 primer design are provided below. Whole genome sequences from closely related strains were used to identify unique target sequences in *B. longum* subsp *longum* CR15. The adenine-specific methyltransferase PaeR71 gene was selected as the target amplicon for *B. longum* subsp *longum* CR15.

TABLE 1

| | |
|---|---|
| Bifidobacterium longum subsp longum KACC 91563, complete genome | CP002794.1 |
| Bifidobacterium longum subsp longum strain AH1206, complete genome | CP016019.1 |
| Bifidobacterium longum subsp longum JCM 1217 DNA, complete genome | AP010888.1 |
| Bifidobacterium longum subsp longum NCIMB809, complete genome | CP011964.1 |
| Bifidobacterium longum subsp longum GT15, complete genome | CP006741.1 |
| Bifidobacterium longum subsp longum BBMN68, complete genome | CP002286.1 |
| Bifidobacterium longum subsp longum CCUG30698, complete genome | CP011965.1 |
| Bifidobacterium longum subsp longum JDM301, complete genome | CP002010.1 |

Genome Sequencing and Assembly of *B. longum* Subsp. *Longum* CR15

For whole genome sequencing, DNA extraction was performed using QIAamp DNA mini kit (Qiagen, Hilden, Germany), and a genomic library was prepared using the Nextera XT DNA Library Prep Kit. The genome of *B. longum* subsp. *longum* CR15 was sequenced on an Illumina MiSeq, resulting in 603,691 paired reads that were assembled de-novo using the SPAdes Genome Assembler (ver 3.11) and aligned against a reference genome using Mauve. A draft genome consisting of 63 contigs with 123-fold coverage was obtained post-assembly.

Gene annotation was performed using PROKKA. Additionally, the draft genome was annotated against the CAZy database using dbCAN and the transportDB 2.0 database through TransAAP to identify carbohydrate active enzyme clusters and sugar transporters, respectively.

Strain-Specific Primer Design and Validation

RUCS (rapid identification of PCR primers for unique core sequences) was used to identify unique targets in the draft genome of *B. longum* subsp. *longum* CR15 and for in-silico PCR. The unique target sequence was identified through alignment with complete genomes of 8 closely related *B. longum* subsp. *longum* strains that were retrieved from the NCBI database.

TABLE 2

| Bifidobacterium strains for primer validation | % identity at 16S rRNA gene level |
|---|---|
| B. longum subsp. longum AH120 | 100% |
| B. longum subsp. longum (ATCC15707) | 99% |
| B. longum longum F8 | 100% |
| B. longum longum JDM301 | 99% |
| B. longum DJ010A | 100% |
| Bifidobacterium sp. 12_1_47BFAA | 100% |
| Bifidobacterium sp. 113 | 95% |
| Bifidobacterium sp. HMLN14 | 96% |

Primer specificity was confirmed by blasting against the NCBI RefSeq representative genome database for bacteria with NCBI Primer Blast. Only 1 hit for a strain of *Gelidibacter algens*, a non-resident of the human gut matched the primer pair. The adenine-specific methyltransferase PaeR71 gene was subsequently selected as the target amplicon with a length of 210 base pairs with the primer pair; forward (F) CCGCATCACAACTGCTATTGG (SEQ ID NO. 3) and reverse (R) CGAAAGCCCCAATTTGTTCGT (SEQ ID NO. 4) (Invitrogen, California, USA). A gradient PCR was used to determine the suitable annealing temperature of 58° C. Experimental primer validation with both PCR and qPCR was performed using 11 strains in our culture collection that had a 95-100% identity at the 16S rRNA level.

TABLE 3

Primer sequences and PCR programs used to target different groups of *Bifidobacterium*.

| Target organism | Primer Direction | Sequence | SEQ ID NO. | qPCR program |
|---|---|---|---|---|
| Bifidobacterium | Forward | TCGCGTCYGGTGTG AAAG | 7 | Initial denaturation at 95° C. for 5 min, 35 cycles at 95° C. for 15 sec, 58° C. for 20 sec, and 68° C. for 30 sec |
| | Reverse | CCACATCCAGCRTC CAC | 8 | |
| B. pseudocatenulatum | Forward | AGCCATCGTCAAGG AGCTTATCGCAG | 9 | Initial denaturation at 95° C. for 5 min, 40 cycles at 94° C. for 15 sec, 68° C. for 15 sec, and 72° C. for 15 sec |
| | Reverse | CACGACGTCCTGCT GAGAGCTCAC | 10 | |
| B. longum | Forward | TTCCAGTTGATCGC ATGGTCTTCT | 11 | Initial denaturation at 95° C. for 10 min, 30 cycles at 95° C. for 15 sec, 65° C. for 1 min, and 72° C. for 45 sec |
| | Reverse | GGCTACCCGTCGAA GCCACG | 12 | |
| B. longum subsp. longum | Forward | CCGCATCACAACTG CTATTGG | 3 | Initial denaturation at 95° C. for 5 min, 30 cycles at 95° C. for 15 sec, 58° C. for 15 sec, and 72° C. for 20 sec |
| | Reverse | CGAAAGCCCCAATT TGTTCGT | 4 | |

Growth Measurement

The ability of selected strains to grow on XOS was performed in mMRS containing 1% XOS. Controls were prepared in mMRS either with 1% glucose (mMRS-glucose) or the equivalent amount of residual carbohydrates present in the 95% pure XOS (about 0.035%, final concentration; mMRS-res). The residual sugars were predicted to be equal proportions of glucose, fructose and sucrose based on the manufacturer's specification sheet. Furthermore, the mMRS media was prepared at half strength (i.e., using only half the amount of ingredients present in standard MRS) in order to minimize growth on background carbohydrates.

Test strains were first streaked onto BSIM plates from frozen stock cultures and incubated for 48 hours anaerobically at 37° C. Single colonies were isolated and inoculated into MRS broth for 24 hours at 37° C. Then, 1% (v/v) of the cultures were transferred into fresh MRS. These subcultures were incubated for 12 hours overnight before they were inoculated at 1% (v/v) into pre-warmed, pre-reduced mMRS, mMRS-XOS, mMRS-glucose, or mMRS-res. Cultures were then incubated anaerobically at 37° C., and growth was determined by measuring the optical density at 600 nm every 4 hours for the first 12 hours and again at 24 hours using a plate reader (Synergy HTX Plate Reader, BioTek, Vermont, USA). All experiments were performed in triplicate.

16S rRNA Amplicon Sequencing and Analysis 16S rRNA amplicon sequencing was performed on DNA extracted from fecal fermentations. Samples were sequenced on a 2×250 bp MiSeq sequencer, using primers for the V4 region of the 16S sequence. A total of 4,397,582 sequences were obtained with a mean of 36,954 sequences per sample.

Sequences were analyzed using QIIME2. Paired-end sequences were de-multiplexed prior to importing into QIIME. FastQC was used to check per sample sequence quality. Using the DADA2 workflow (found on the web at benjjneb.github.io/dada2/), chimeric sequences were removed and forward and reverse reads were truncated to 240 bp and 200 bp, respectively. Sequences were de-replicated into unique amplicon sequence variants (ASV) with DADA2, and a list of exact representative sequences were created. ASV refers to the exact sequences that are resolved through the DADA2 pipeline, as described previously. The resulting product is an ASV table recording the number of times by which an ASV was observed in each sample. A total of 974 features were identified. Taxonomy was assigned using the Greengenes database with the pre-trained classifier based on 99% sequence identity. Alpha diversity measures were calculated using a sample depth of 5171 sequences.

Statistical analysis for community sequencing data was done in QIIME and RStudio (ver 3.4.3). Two different alpha diversity measurements; Shannon index and Observed ASVs were computed. Pairwise comparisons between each treatment and time-point were made using Kruskal-Wallis test. FDR correction was incorporated for all statistical tests, and significance was determined using significance cutoff at 0.05. For beta diversity, Principal Coordinates Analysis (PCoA) and Principal Component Analysis (PCA) plots were prepared to compare community composition. The vegan (found on the web at github.com/vegandevs/vegan) package was used to compute Bray Curtis distance and conduct PERMANOVA analysis. Comparisons of the relative abundances of specific ASVs between XOS treatments at 96 hours were conducted using Wilcoxon rank sum test and visualized using Metacoder. Only taxa that had a relative abundance of greater than 0.1% were included in the analysis.

Short/Branched Chain Fatty Acids (S/BCFA) Analysis

S/BCFA concentrations were determined for all 20 fecal samples at all sample times using gas chromatography, similar to Yang and Rose. Briefly, 0.4 ml of fermentation supernatant was vortexed with approximately 0.16 g of NaCl and 0.2 ml of 9M sulfuric acid. Subsequently, 0.5 ml of diethyl ether was added, and tubes were shaken and briefly centrifuged. Then, 1 μl of the extract was injected into a gas chromatograph (Clarus 580; PerkinElmer, Waltham, Mass., USA) with a fused silica capillary column (Nukol 30 m×0.25 mm inner diameter×0.25 μm film thickness; Sigma-Aldrich, St. Louis, Mo., USA). Quantification of S/BCFA was carried out as described previously. Six samples could not be quantified due to insufficient amount of analyte. Subjects that comprised of any of these samples were removed and S/BCFA concentrations for 14 out of 20 subjects were used for the final statistical analysis. For comparison between treatments at every time point, a Kruskal Wallis test was conducted along with Wilcoxon rank sum test with FDR adjustment.

PICRUSt was used to relate taxonomic abundances from 16S data to functional S/BCFA metabolic genes, based on the Kyoto Encyclopedia of Genes and Genomes (KEGG) Ontology database. Correlation analysis between taxa and S/BCFA was also performed using the 16S sequencing data and all available S/BCFA concentrations. In addition, mean relative abundances of taxa and S/BCFA predicted metabolic genes were visualized for each treatment.

Results

Enrichment of XOS-Utilizing *Bifidobacterium* Strains

Figure 1B:
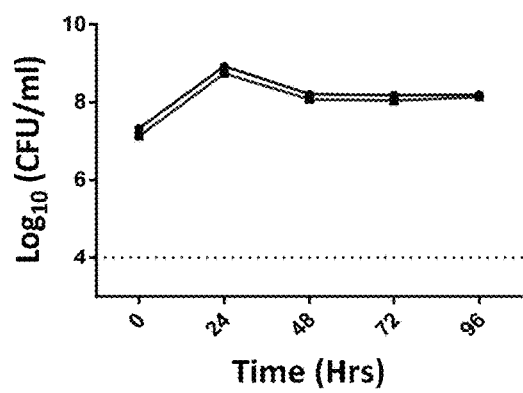
FIG. 1B is a graph illustrating enrichment of total *Bifidobacterium* (●) and *B. adolescentis* (■) in a sample from which *B. adolescentis* CR11 was isolated, wherein the Bifidobacteria was enriched by XOS in fecal environments whereas strain establishment was dependent on the strain and the host.

A total of 60 bifidobacteria isolates were initially obtained from enrichment experiments using 3 different fecal donor samples. A successful enrichment would be predicted by an increase or recovery of specific species of bacteria after every step-wise 100-fold dilution (FIG. 1A). Strains that were not enriched would be expected to be present at low abundance or entirely washed out (below detection levels) at the end of the four fermentation cycles (about 25 generations). From the 60 isolates obtained, identification through BLASTn of the 16S rRNA Sanger-based sequences resulted in 7 unique bifidobacteria strains. These included five strains of *B. adolescentis* and one each of *B. pseudocatenulatum* and *B. longum*. Quantification at the genus level using qPCR revealed enrichment of total *Bifidobacterium* in all 3 samples. Specifically, one *B. adolescentis* isolate was obtained from a sample displaying enrichment in species of *B. adolescentis* (FIG. 1B), and this isolate, *B. adolescentis* CR11 was chosen for subsequent establishment experiments.

Establishment of *B. adolescentis* CR11 and Surprising Discovery of *B. longum* Subsp. *Longum* CR15

Figure 1C:
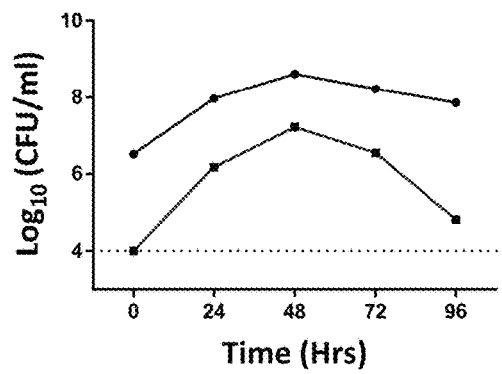
FIG. 1C is a graph illustrating the unsuccessful establishment of *B. adolescentis* CR11 (■) with commensurate enrichment of total *Bifidobacterium* (●) enriched by XOS in fecal environments whereas strain establishment was dependent on the strain and the host.

The ability of a strain to become established in an in vitro fecal environment was assessed in establishment experiments in a manner similar to that of the XOS enrichment, except that the test strain was included along with the prebiotic. A successful establishment was denoted by persistence of the test strain during the test period, whereas a failed establishment was indicated by a decrease in abundance or washout of the test strain over the test period. When *B. adolescentis* CR11 was reintroduced in a new fecal sample along with the prebiotic at the start of fermentation, quantification by genus-specific qPCR revealed that enrichment of *Bifidobacterium* was initially observed (FIG. 1C). Surprisingly, based on species-specific qPCR, it was evident that *B. adolescentis* had been displaced by other bifidobacteria. Indeed, all of the isolates (n=10) subsequently recovered by culturing were identified as *B. longum* by 16S Sanger sequencing.

Figure 1D:
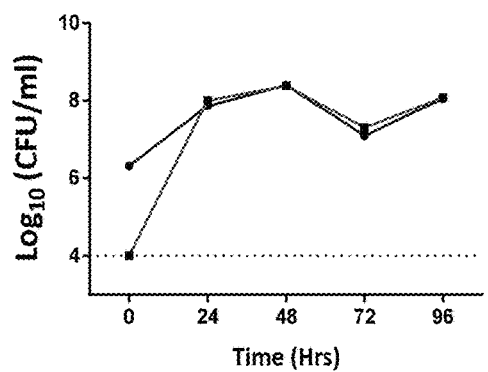
FIG. 1D is a graph illustrating the establishment of *B. longum* subsp. *longum* CR15 (■) and total *Bifidobacterium* (●). Horizontal dashed lines indicate limits of detection ($10^4$ CFU/mL) and the *Bifidobacterium* was enriched by XOS in fecal environments whereas strain establishment was dependent on the strain and the host.
Figure 2:
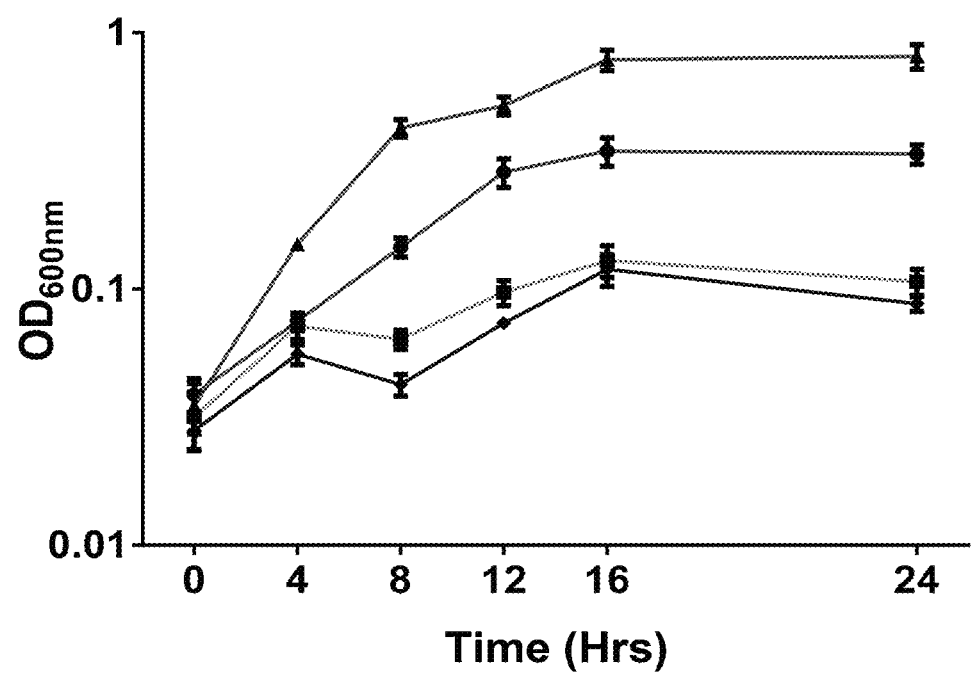
FIG. 2 is a graph illustrating the growth of *B. longum* subsp. *longum* CR15 in minimal media supplemented with sugars. Optical density measurements at a wavelength of 600 nm were taken at 4-hour periods within the first 16 hours and again at 24 hours in mMRS (♦) and in mMRS containing the equivalent amounts of residual sugars in the XOS (■), 1% glucose (▲), 1% XOS (•); 1% XOS DPs 2,3,4 ( ⬤ ) and 1% XOS DP≥4 (▼).

The *B. longum* strain (identified and named as *B. longum* subsp. *longum* CR15) was subsequently introduced into another fecal sample. Quantification revealed stable enrichment of *B. longum* species, with 100% of the isolates (n=10) identified as *B. longum* (FIG. 1D). Growth of *B. longum* subsp. *longum* CR15 in mMRS-XOS demonstrated that this strain was able to utilize XOS with a preference for polymers with a low degree of polymerization.

Genome Assembly and Annotation of *B. longum* Subsp. *Longum* CR15

Whole genome sequence data was generated (a total of 296 Mbp), and a draft genome of 2.4 Mbp was assembled with 96% coverage against a reference genome. Annotation against the CAZy database identified several proteins associated with XOS utilization, including the glycosyl hydrolases, GH43 and GH120 and carbohydrate binding molecules, CBM6 and CBM22. In addition, relevant sugar transport and utilization genes were annotated with Prokka and TransAAP as D-xylulose 5-phosphate (xfp), xylose isomerase (xylA), xylulokinase (xylB), (3-xylosidase (xynB), xylose import ATP-binding protein (xylG), xylose transport system permease protein (xylH) and ABC-type xylose transport system (xylF). Strain specific primers targeting the adenine-specific methyltransferase PaeR71 gene were subsequently designed from the genome.

Establishment of *B. longum* Subsp. *Longum* CR15 is Host-Dependent

Figure 3:
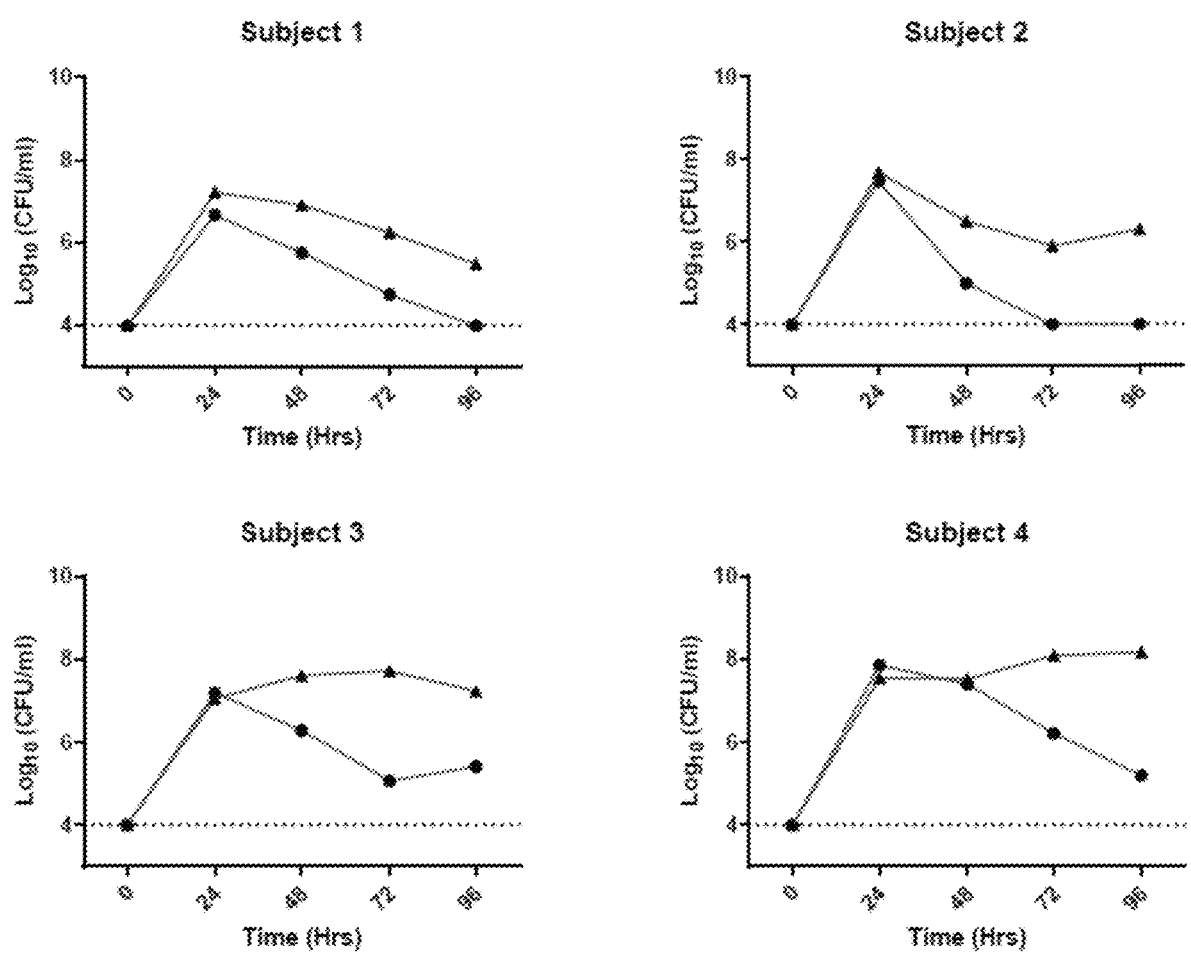
FIG. 3 is a series of graphs illustrating the establishment of *B. longum* subsp. *longum* CR15 after inoculation into 20 individual fecal samples in the presence (▲) or absence (•) of XOS. For each experiment, the strain was inoculated at $10^7$ CFU/mL and quantified by RT-qPCR using strain-specific primers. Horizontal dashed lines indicate the limit of detection ($10^4$ CFU/mL)
Figure 3:
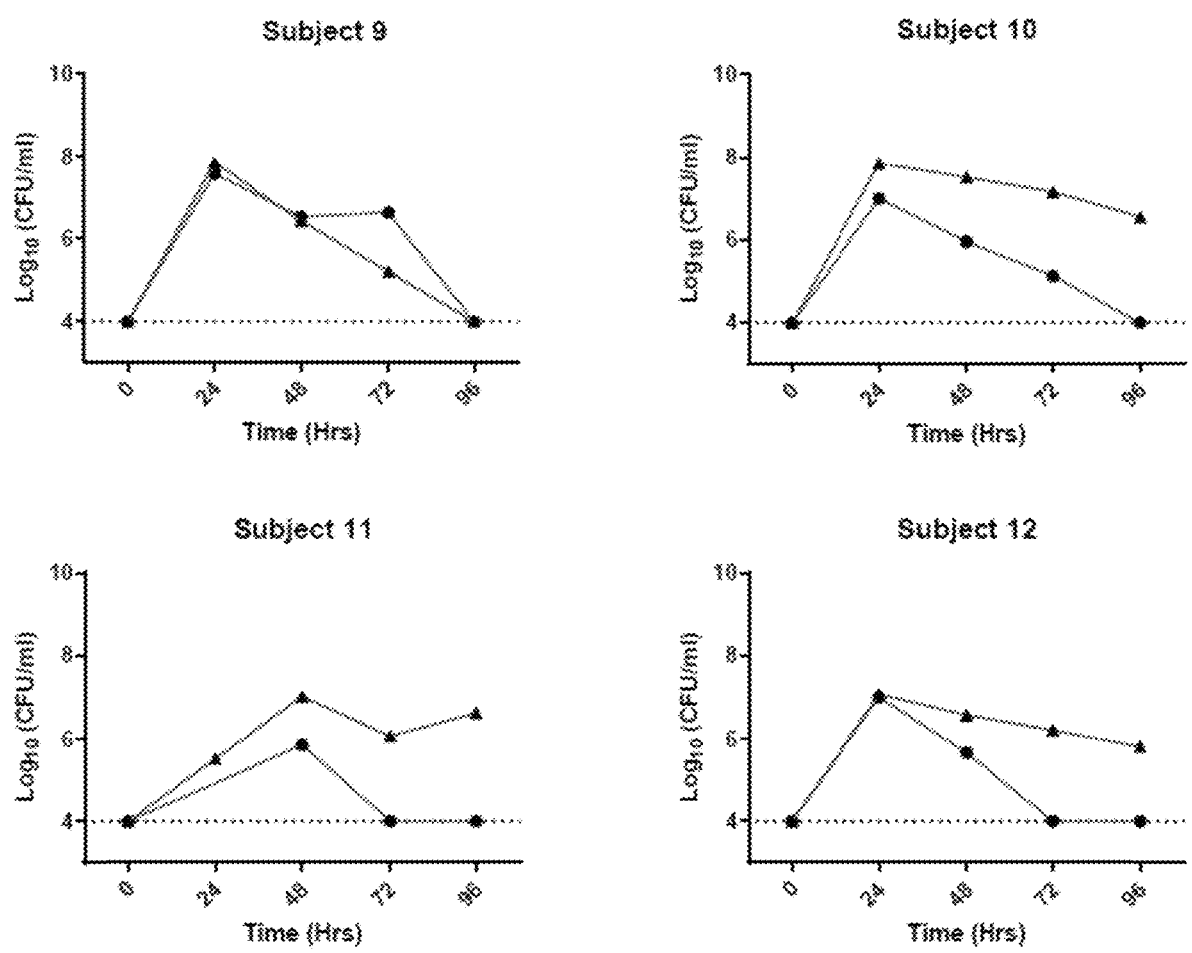
Figure 3:
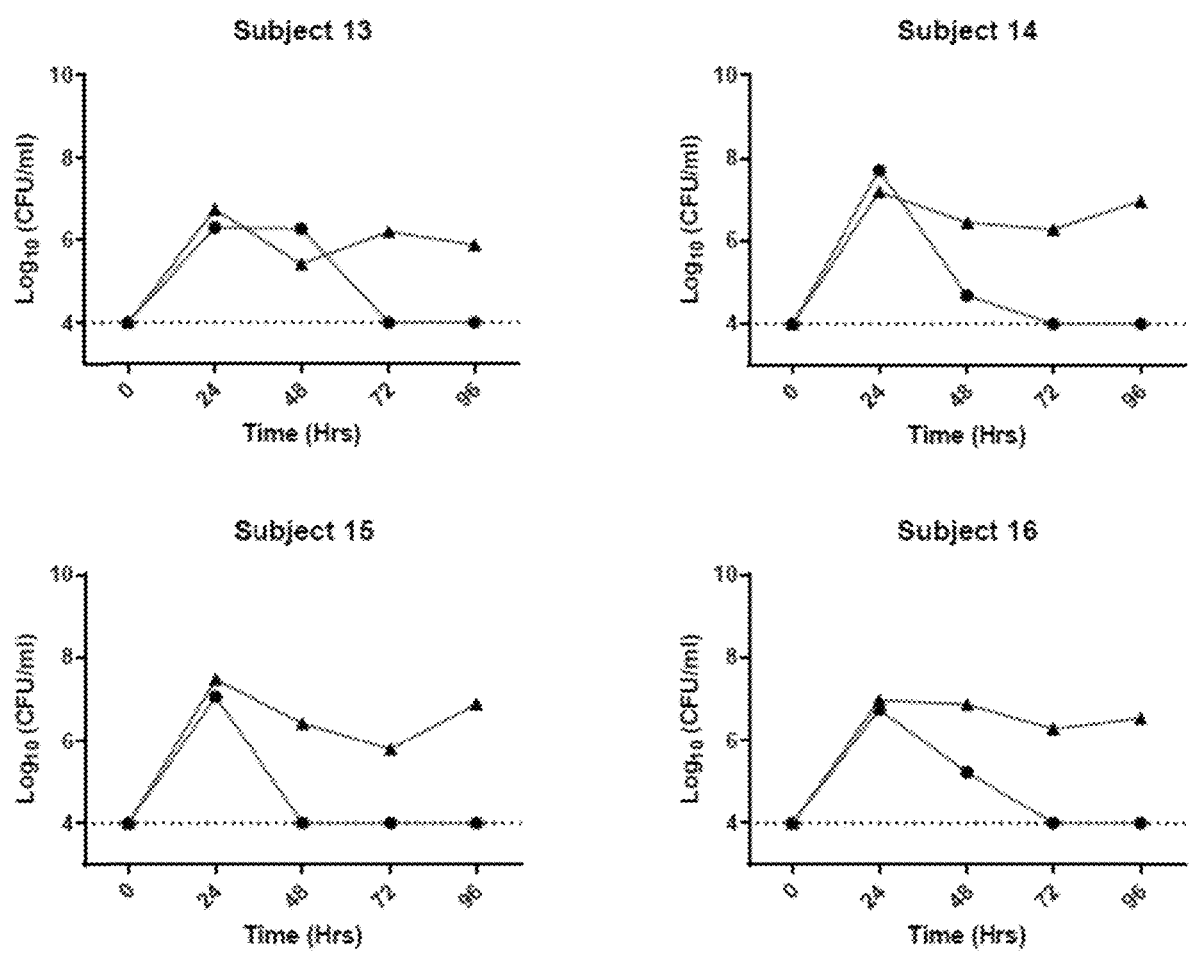
Figure 3:
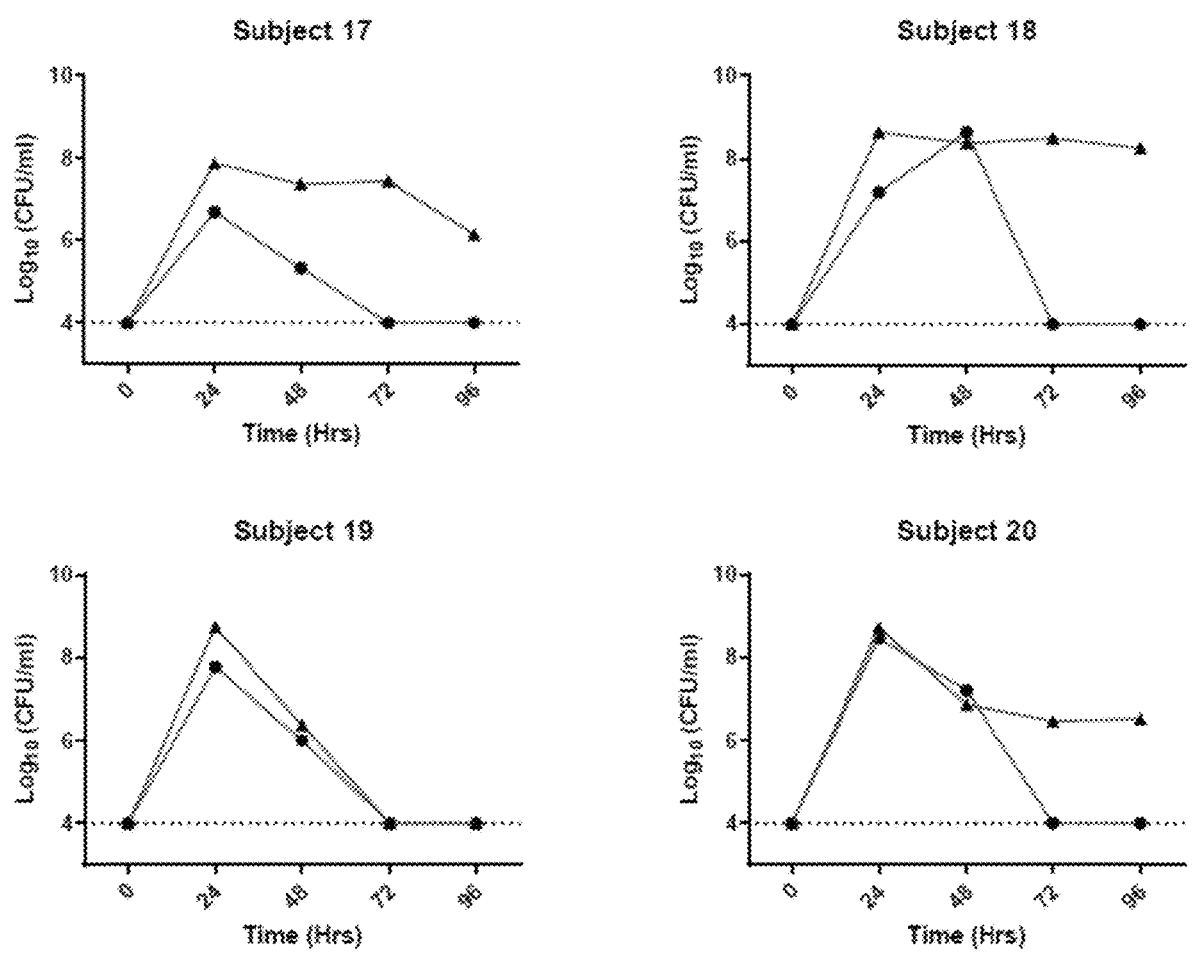

Additional establishment experiments with *B. longum* subsp. *longum* CR15 and XOS were performed using 20 individual donor samples. Experiments in the absence of XOS were conducted in parallel and served as controls. In the presence of XOS, strain-specific qPCR quantification revealed that the CR15 strain was clearly established in 7 samples; another 11 demonstrated intermediate establishment (FIG. 3, 4A-B). The latter included samples in which CR15 levels fluctuated between the start and end of fermentation or decreased by less than 2 logs (FIG. 4C). Only in two samples did the CR15 strain fail to become established (FIG. 4D). *B. longum* subsp. *longum* CR15 was either reduced or completely washed out in the no-prebiotic-containing controls.

XOS Treatment Differentially Shifts the Fecal Microbial Community

Figure 5A:
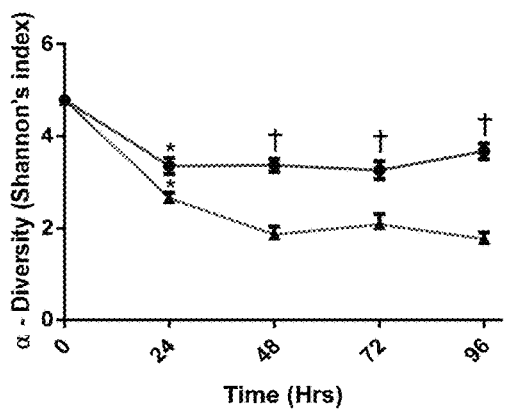
FIG. 5A is a graph illustrating an analysis of microbial community composition and diversity across treatments using the Shannon measure of α-diversity.
Figure 5B:
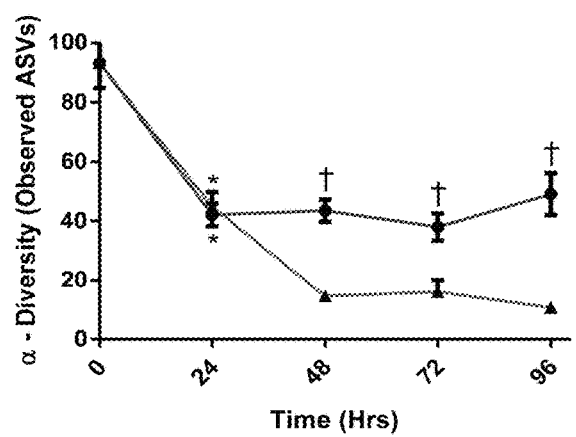
FIG. 5B is a graph illustrating an analysis of microbial community composition and diversity across treatments using the number of ASV's measure of α-diversity.
Figure 5C:
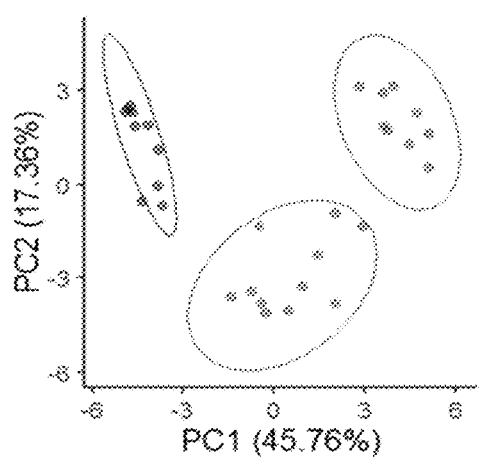
FIG. 5C is a graph illustrating Principal Coordinate Analysis (PCoA); and revealing distinct community profiles between groups at baseline (blue) and at the end of the fermentation period, with (green) or without (red) XOS (PERMANOVA, p=0.001). * indicates significant difference between 0 and 24 hours. † indicates significant differences between treatments at a particular timepoint.
Figure 5D:
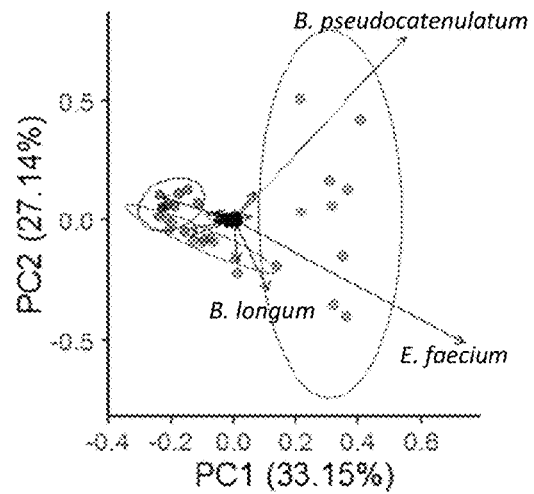
FIG. 5D is a graph illustrating Principal Component Analysis (PCA) and revealing distinct community profiles between groups at baseline (blue) and at the end of the fermentation period, with (green) or without (red) XOS (PERMANOVA, p=0.001). * indicates significant difference between 0 and 24 hours. † indicates significant differences between treatments at a particular timepoint.

Next, 16S amplicon sequencing was performed to investigate changes in community structure in a subset of 10 samples. To assess alpha diversity of the samples over time, Shannon's index and observed amplicon sequence variants (ASVs) were computed. There was an initial significant decrease in diversity (FDR<0.05) from 0 to 24 hours for both treatments (FIG. 5A-B). However, no further changes were observed after the first 24-hour time point. Throughout the fermentation period, the diversity of the XOS supplemented samples were significantly lower than the no-prebiotic controls (FDR<0.05). Beta diversity analysis of the samples at baseline and at the end of fermentation was visualized using Principal Coordinate Analysis (PCoA) based on Bray-Curtis distance. The samples at baseline clustered together while fermentation samples at 96 hours clearly clustered separately based on treatment (FIG. 5C). Principal Component Analysis (PCA) revealed that *B. longum*, *B. pseudocatenulatum* and *Enterococcus faecium* were drivers in the XOS group (FIG. 5D).

Figure 6A:
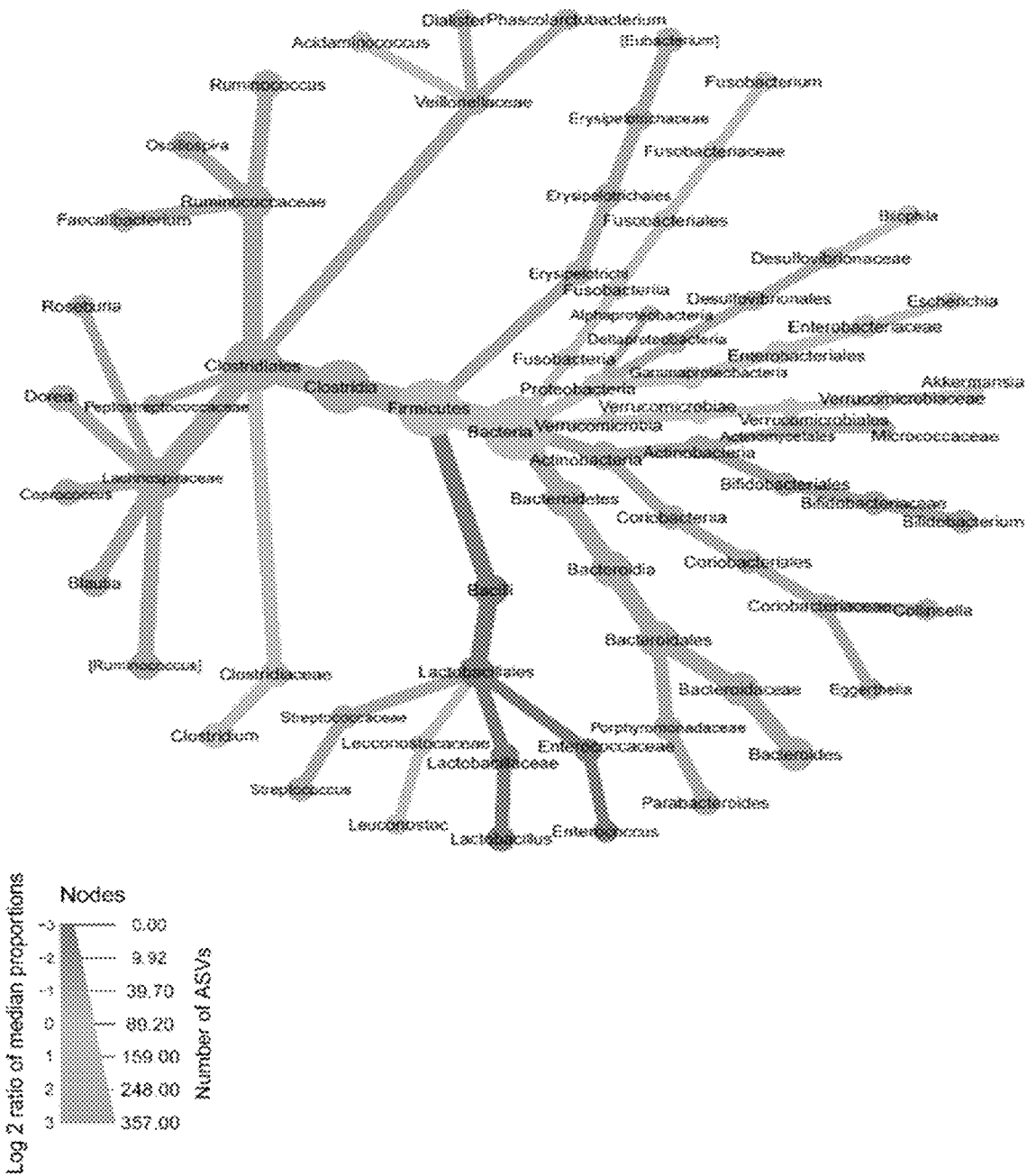
FIG. 6 illustrates significant changes in taxa driven by XOS in establishment experiments with *B. longum* subsp. *longum* CR15. Wilcoxon rank sum test with FDR adjustment was used to identify significantly different taxa (FDR<0.05) in the presence (A) and absence (B) of XOS. Nodes in orange indicate greater abundance at baseline compared to 96 hours whereas nodes in green and red indicate greater abundance at 96 hours compared to baseline.
Figure 6B:
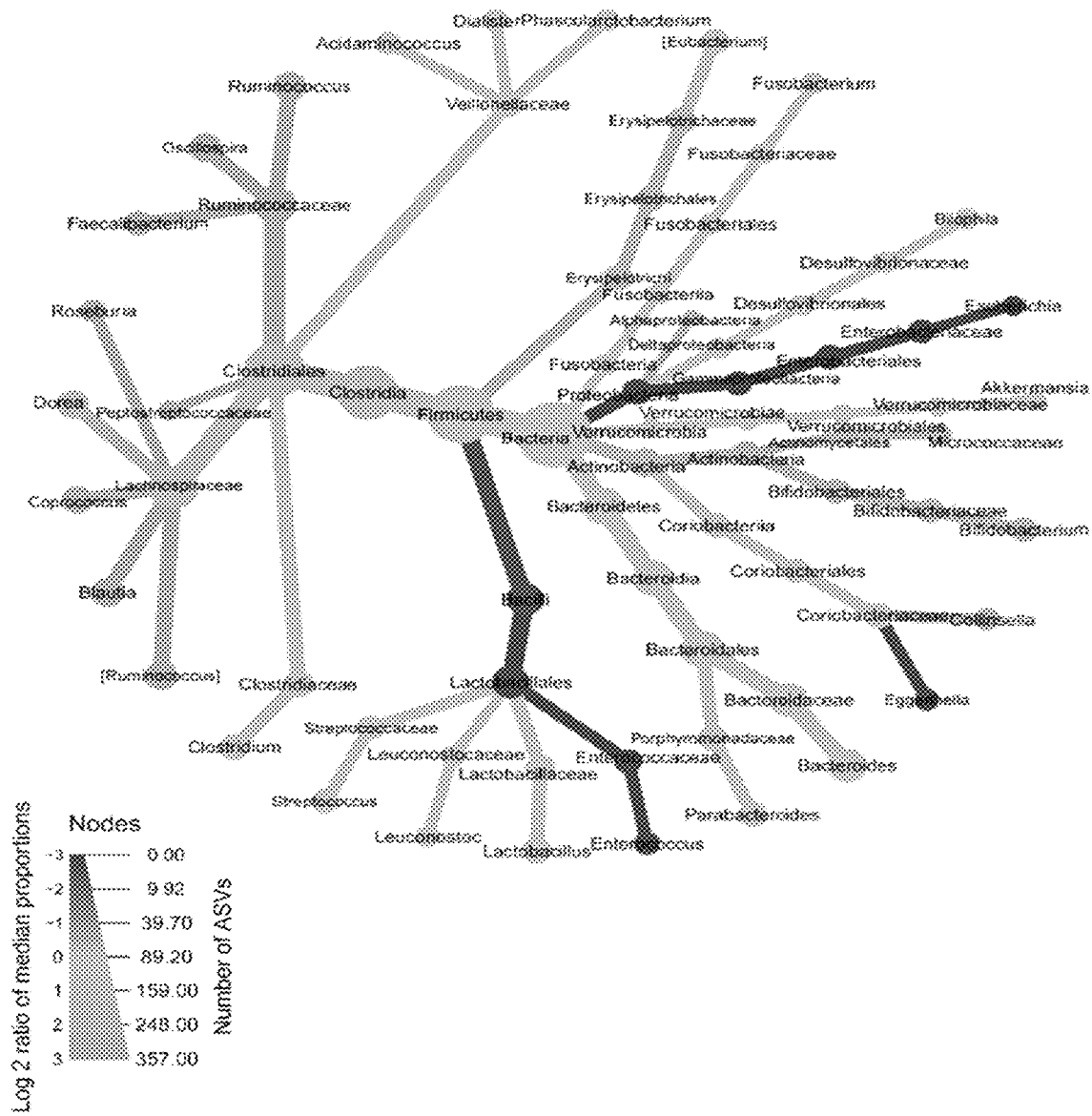

Taxonomic analysis of the 16S rRNA sequences revealed a highly bifidogenic response in the presence of XOS as well as significant enrichment of *Lactobacillus* that was not observed in the no-XOS controls (FIG. 6A). Enrichment of *Enterococcus* was also observed after 96 hours for both the XOS and no-XOS treatments (FIG. 6A-B). Three specific *Bifidobacterium* ASVs were investigated for their contribution towards the bifidogenic response throughout the fermentation duration (FIG. 7A-C). BLASTn of these specific sequence variants against the NCBI nr database revealed that they belonged to the species *B. longum*, *B. pseudocatenulatum* and *B. adolescentis*. These species were also previously observed from the 16S Sanger sequencing of isolates that were obtained post-fermentation.

Co-Enrichment of *B. longum* Subsp. *Longum* CR15 and *B. pseudocatenulatum*

Additional analyses revealed differences in the mean abundance of the *B. longum* and *B. pseudocatenulatum* ASVs between treatments. In the first 24 hours, the mean percentage relative abundance of the *B. longum* ASV increased from 4% to 43% in fermentations with XOS but only to 11% in the no-prebiotic controls (FIG. 7A). While a subsequent decrease in abundance of the *B. longum* ASV was observed in both treatments, only 1% remained at 96 hours in the controls compared to 10% in the XOS fermentations (FIG. 7A). In addition, there was an average increase from 4% to 29% in the *B. pseudocatenulatum* ASV in the XOS-supplemented fermentations after 96 hours (FIG. 7B). Low abundance of the *B. adolescentis* ASV was observed throughout the fermentation in both XOS and no-XOS treatments (FIG. 7C).

The effect of *B. pseudocatenulatum* on persistence of CR15 was determined by species-level qPCR. In most cases (n=11), when *B. pseudocatenulatum* was absent (i.e., below detection) in fecal samples at baseline, levels remained low throughout fermentation and successful establishment of *B. longum* subsp. *longum* CR15 was observed (FIG. 8B). In contrast, *B. pseudocatenulatum* was able to persist and co-occur with CR15 if detectable levels of this organism were present at baseline (n=9) (FIG. 8A).

Figure 10A:
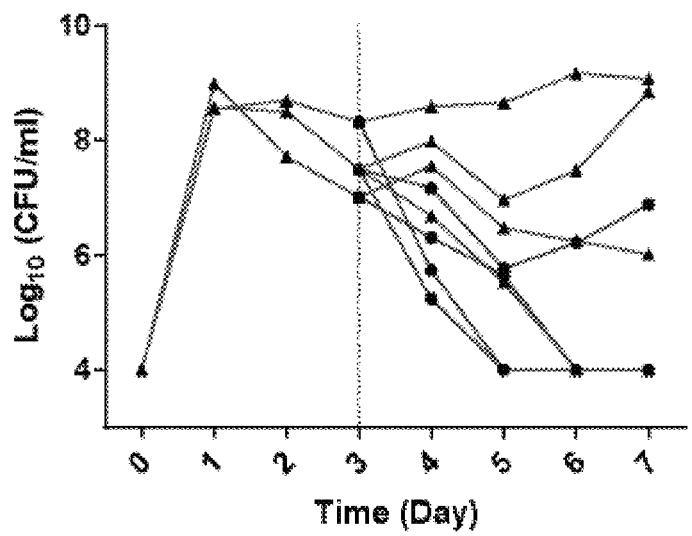
FIG. 10A is a graph illustrating qPCR quantification of *B. longum* subsp *longum* CR15 throughout fermentation with (▲) and without (•) XOS in the 4 samples tested.
Figure 10B:
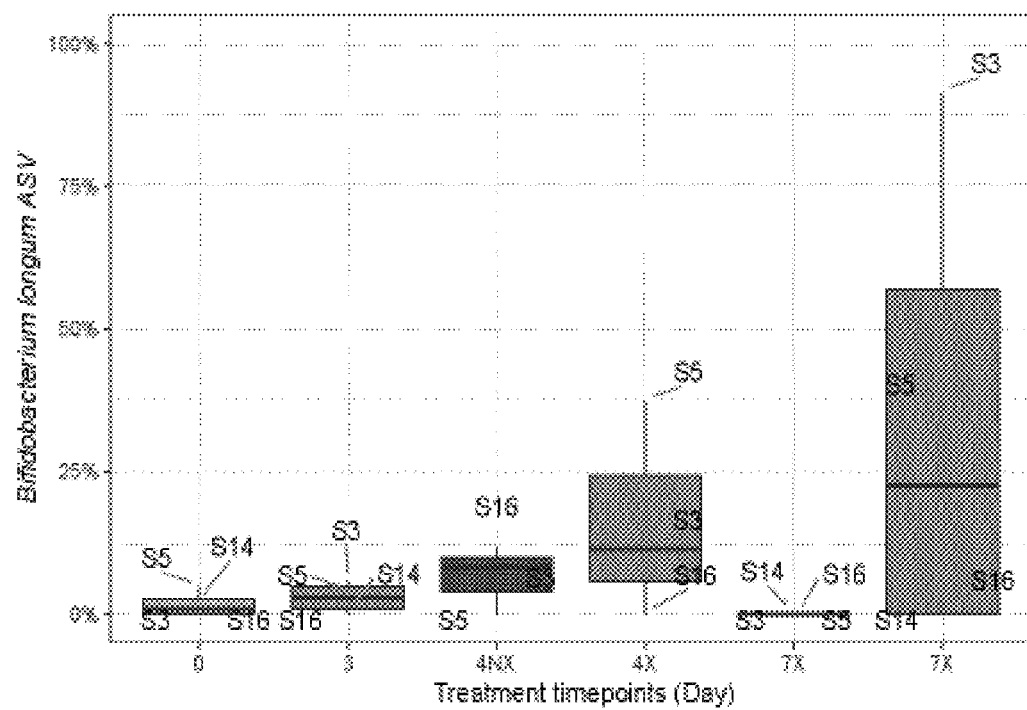
FIG. 10B is a graph illustrating the relative abundance of *B. longum* in the presence of XOS at each time point, wherein 0 is the baseline of samples at the start of fermentation, NX is fermentation without XOS, X is fermentation with XOS, and wherein day 4 samples for S14 were not sequenced and ▲; +XOS, •; −XOS.
Figure 10C:
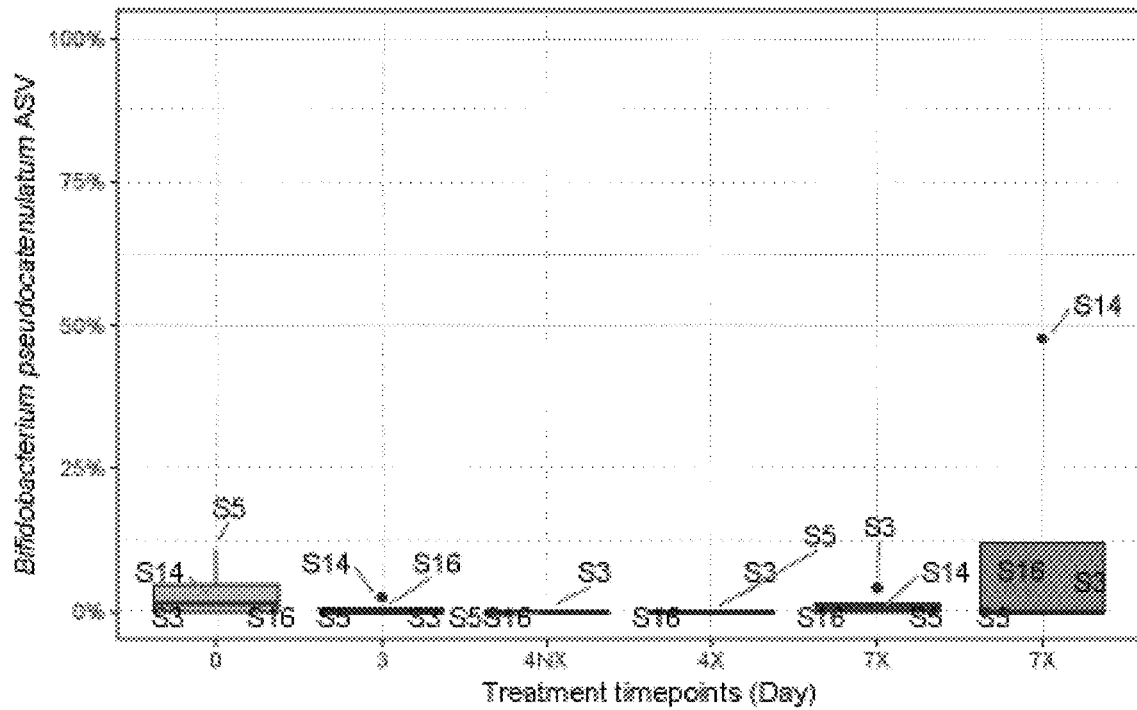
FIG. 10C is a graph illustrating the relative abundance of *B. pseudocatenulatum* in the presence of XOS at each time point, wherein 0 is the baseline of samples at the start of fermentation, NX is fermentation without XOS, X is fermentation with XOS, and wherein day 4 samples for S14 were not sequenced and ▲; +XOS, •; −XOS.
Figure 10D:
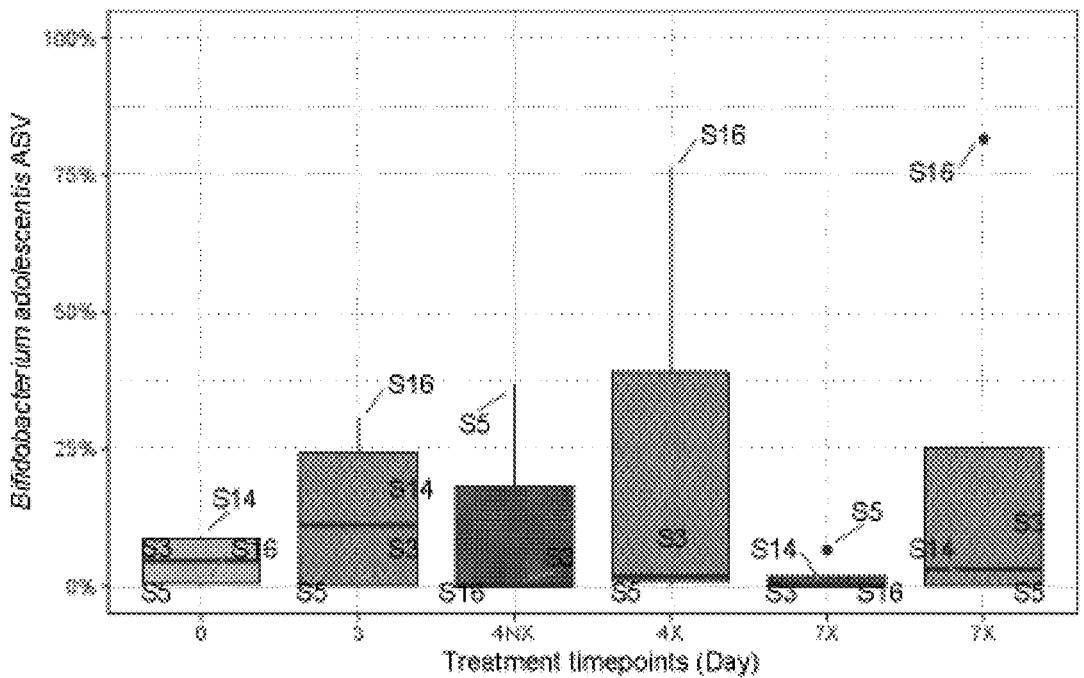
FIG. 10D is a graph illustrating the relative abundance of *B. adolescentis* in the presence of XOS at each time point, wherein 0 is the baseline of samples at the start of fermentation, NX is fermentation without XOS, X is fermentation with XOS, and wherein day 4 samples for S14 were not sequenced and ▲; +XOS, •; −XOS.

To further investigate the persistence potential of *B. longum* subsp. *longum* CR15, a 7-day washout experiment was performed using a subset of 4 of the 20 fecal samples. In 2 samples (Subjects 3 and 4), high numbers of *B. longum* subsp. *longum* CR15 were maintained through day 7. However, in the other 2 samples (Subjects 14 and 16), *B. longum* subsp. *longum* CR15 were decreased or washed out by day 7, even in the presence of XOS (FIG. 10A,B). Subsequent 16S amplicon sequencing of these day 7 samples revealed high abundance of two ASVs corresponding to *B. adolescentis* and *B. pseudocatenulatum* (FIG. 10 C,D). This 7 day fermentation experiment further demonstrates dependency of *B. longum* subsp. *longum* CR15 on XOS along with host-dependent response. Samples were first supplemented with XOS and stepwise transfers were carried out for the first 3 days. A split was done during day 3 with parallel transfers into XOS-containing fermenters and in fermenters without XOS. Subsequent step-wise transfers were conducted from day 4 to day 7 following the respective treatments at the split. 16S sequencing was carried out for samples for Days 0, 3, 4, and 7. The 16S RNA sequence for *B. longum* subsp. *longum* CR15 is SEQ ID NO. 13 and the 16S RNA sequence for *B. pseudocatelenatum* CR16 is SEQ ID NO. 14.

Acetate is Enriched in XOS-Supplemented Fermentations

Short and branched chain fatty acid (S/BCFA) profiles were obtained for all 20 *B. longum* subsp. *longum* CR15 establishment experiments in the presence and absence of XOS. At all time points, acetate levels were highest, followed by lower levels of propionate and butyrate (Table 4). At 24 hours, acetate and total SCFA levels were significantly higher in the prebiotic group, whereas by 48 hours, butyrate and propionate levels were significantly higher in the control group. By 96 hours, the BCFAs, isobutyrate and isovalerate, were significantly higher in the control group. After 24 hours, SCFA production remained generally stable for both treatments.

TABLE 4

Concentrations of S/BCFA from fermentation supernatants of establishment experiments with *B. longum* subsp. *longum* CR15.

| Microbial metabolite | 0 h | mean S/BCFA concentration (mM) ± SEM | | | | | | |
|---|---|---|---|---|---|---|---|---|
| | | 24 h | | 48 h | | 72 h | | 96 h | |
| | | Control | XOS | Control | XOS | Control | XOS | Control | XOS |
| Acetate | 8.72 ± 3.61 | 18.65 ± 2.35 | 34.94 ± 3.73†* | 11.65 ± 2.18 | 33.64 ± 3.69† | 8.94 ± 1.26 | 41.25 ± 5.03† | 11.59 ± 1.87 | 42.24 ± 2.85† |
| Butyrate | 0.05 ± 0.01 | 0.69 ± 0.21* | 0.53 ± 0.26 | 1.04 ± 0.21 | 0.48 ± 0.18† | 1.07 ± 0.23 | 0.43 ± 0.21 | 0.94 ± 0.19 | 0.35 ± 0.18† |
| Propionate | 0.09 ± 0.05 | 0.5 ± 0.33 | 0.39 ± 0.19 | 1.35 ± 0.22* | 0.06 ± 0.03† | 1.24 ± 0.23 | 0.04 ± 0.02† | 1.46 ± 0.20 | 0.05 ± 0.02† |
| Total SCFA | 8.87 ± 3.64 | 19.84 ± 2.60* | 35.85 ± 3.38†* | 14.04 ± 2.39 | 34.18 ± 3.67† | 11.25 ± 1.61 | 41.72 ± 5.04† | 13.99 ± 1.84 | 42.64 ± 2.85† |
| Isobutyrate | 0.01 ± 0.003 | 0.01 ± 0.004 | 0.02 ± 0.01 | 0.07 ± 0.04 | 0.01 ± 0.01 | 0.05 ± 0.02 | 0.003 ± 0.001 | 0.11 ± 0.05 | 0.01 ± 0.004† |
| Isovalerate | 0.02 ± 0.003 | 0.02 ± 0.01 | 0.17 ± 0.12 | 0.21 ± 0.09 | 0.18 ± 0.14 | 0.38 ± 0.18 | 0.29 ± 0.25† | 0.19 ± 0.06 | 0.04 ± 0.02† |
| Total BCFA | 0.02 ± 0.005 | 0.03 ± 0.01 | 0.18 ± 0.12 | 0.27 ± 0.11 | 0.19 ± 0.14 | 0.43 ± 0.19 | 0.3 ± 0.25† | 0.3 ± 0.11 | 0.05 ± 0.02† |

Figure 9:
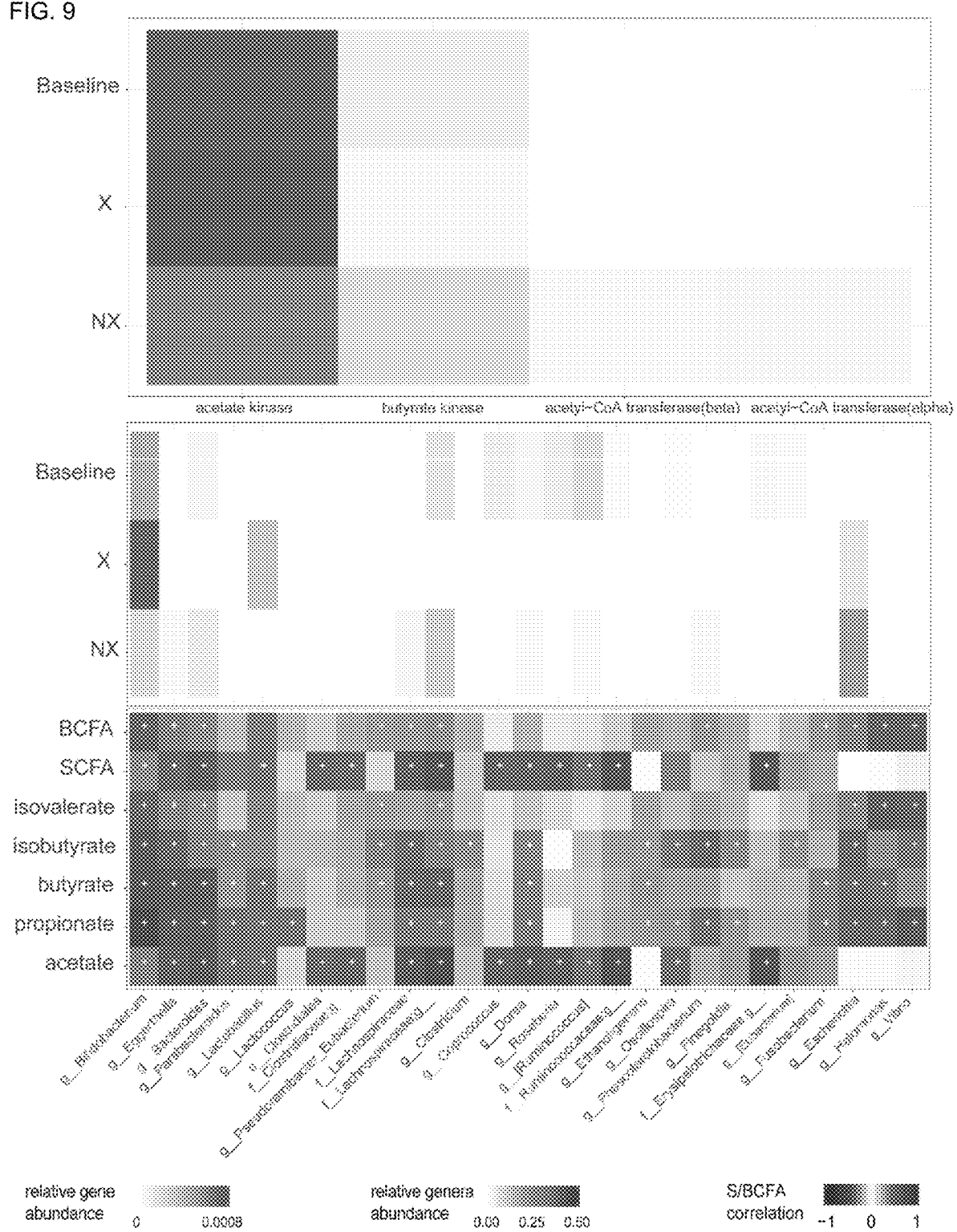
FIG. 9 is a set of graphs illustrating mean relative abundances for taxa and predicted S/BCFA genes and correlation of microbial fermentation metabolites with genera identified in the fermentation samples. Only genera that had at least one significant correlation with a metabolite were mapped. +significant correlation between genus abundance and concentration of metabolite (FDR<0.05). SCFA; short chain fatty acids, BCFA; branched chain fatty acids, X; XOS, NX; No XOS.

SEM; standard error of mean
*denotes significant difference than the previous timepoint
†denotes significant difference between XOS and control treatments within a timepoint.
SCFA; short chain fatty acids, BCFA; branched chain fatty acids PICRUSt was used to assess differences in the abundance of predicted metabolic genes involved in acetate and butyrate production between treatments. Specifically, butyrate kinase, acetate kinase and acetyl-CoA transferase genes were investigated. As expected, metagenome predictions indicated higher levels of acetate kinase genes in the XOS group. Likewise, higher levels of butyrate kinase and acetyl-CoA transferase genes in the control group were also predicted (FIG. 9). Further investigation of family-level taxonomic contributions towards those genes suggested that Prevotellaceae, Paraprevotellaceae, Bacteroidaceae and Rikenellaceae contributed towards butyrate kinase. A total of 11 and 46 taxa were identified to contribute towards acetyl-CoA transferase and acetate kinase, respectively. Among those, taxa that contributed towards acetate kinase were Bifidobacteriaceae and Lactobacillaceae while Enterobacteriaceae, Lachnospiraceae, Ruminococcaceae were identified as contributors of acetyl-CoA transferase. Correlation analysis between genera abundance and S/BCFA concentrations confirmed significant positive correlation between *Bifidobacterium* and *Lactobacillus* with acetate (FIG. 9). *Eggerthella, Bacteroides* and Lachnospiraceae were among several genera that were positively correlated with butyrate and propionate.

The whole genome sequence of *B. longum* subsp. *longum* CR15 (SEQ ID NO. 5) is uploaded in the NCBI database at PRJNA540282 and PRJNA540304, respectively and 16S rRNA sequencing of fermentation samples are uploaded in the NCBI database and can be found at PRJNA540282 and PRJNA540304, respectively.

Discussion

In this study, we developed an in vitro enrichment (IVE) platform for isolating prebiotic-enriched strains that could be combined with the cognate prebiotic to form synergistic synbiotics. Enrichment was performed using a bifidogenic and highly selective substrate, XOS. Overall, 15 unique *Bifidobacterium* isolates were obtained. All belonged to one of three species, *B. pseudocatenulatum, B. longum*, and any extract or combination thereof *B. pseudocatenulatum*, and *B. longum*, which are among the predominant resident *Bifidobacterium* species found in adults. Of these 3 species, *B. adolescentis* and *B. longum* have been well studied for their probiotic properties, as well as for their growth potential on XOS. In contrast, the probiotic potential of *B. pseudocatenulatum* has not been well explored. However, it is known to ferment dietary fibers, including XOS.

Compared to strain enrichment by prebiotics, strain establishment is a more complex and challenging process. Indeed, probiotic microbes rarely persist after the supplementation period has ended. This is due, in part, to the individuality and highly competitive nature of the gut microbiome, as well as the absence of open ecological niches. These factors likely contribute to the responder/non-responder phenomenon that is commonly observed in dietary intervention studies. Thus, the absence of an available ecological or functional niche could inhibit or prevent the establishment of a particular strain.

In contrast, provision of a prebiotic or other specialized nutrient, along with a suitable probiotic, could provide a new nutrient niche, enhance persistence, and reduce the frequency of non-responder phenotypes. In this in vitro study, combining the XOS-enriched *B. longum* subsp. *longum* CR15 strain with XOS promoted strain establishment in most of the 20 unique fecal samples, with steady-state populations maintained at about $10^7$ CFU/ml. Although variation in the persistence phenotype was observed, the CR15 strain was unable to persist in only two samples. XOS-dependent establishment was confirmed by the rapid washout of CR15 in fermentations in the absence of the prebiotic.

While qPCR was useful for measuring populations of specific genera, species, or strains, community sequencing provided an independent basis for assessing changes in microbial composition. Taxonomic results confirmed that enrichment of *B. longum* occurred as a result of XOS supplementation. This observation also suggested that a specific *B. longum* ASV that was present in high abundance was representative of the CR15 strain, although it may be comprised of other closely related *B. longum* strains that shared high 16S sequence similarity.

Interestingly, community analysis also revealed that the *B. longum* ASV/CR15 strain was not always the dominant *Bifidobacterium*. In some samples, *B. pseudocatenulatum* and *B. pseudocatenulatum*, as represented by two other unique ASVs, were prevalent during the fermentations, and their growth was clearly supported by the presence of XOS. In particular, *B. pseudocatenulatum* was present in high abundance across multiple samples. This was further confirmed by qPCR showing that levels of *B. pseudocatenulatum* remained high during the entire fermentation when present at baseline. Both methods suggested that *B. pseudocatenulatum* was also enriched by XOS. In some samples, an observed relative low abundance/absence of *B. longum* subsp. *longum* when *B. pseudocatenulatum* abundance was high suggested these two microbes were niche competitors.

The synbiotic treatment led to significantly lower alpha diversity measures, likely due to enrichment of bifidobacteria. This was further confirmed in the PCA plot where *Bifidobacterium* was a major driver differentiating the two treatments. Reduced diversity has been previously observed in in vitro studies of fiber fermentation.

When the step-wise fermentations were extended to seven days, CR15 again persisted in the presence of XOS for the first 4 days. However, beyond day 4, persistence was more variable. When CR15 was washed out, increased populations of *B. adolescentis* and *B. pseudocatenulatum* were observed.

SCFAs are beneficial by-products of gut metabolism that are associated with carbohydrate fermentation. Like other SCFAs, acetate serves as an energetic source for epithelial cells and comprises a high percentage of total SCFA produced in the gut. In the presence of XOS, the higher concentrations of acetate were likely due to fermentation by *Bifidobacterium* although it is possible that enriched lactobacilli (FIG. 6A) may have also produced acetate. However, the low butyrate levels were unexpected. This is because high abundance of bifidobacteria usually correlates with butyrate production via metabolic cross-feeding between acetate-producing bifidobacteria and acetate-consuming butyrate producers. In particular, Rivière et al. (2015) demonstrated both bifidogenic and butyrogenic effects of arabinoxylan oligossacharides (AXOS) in co-culture fermentations with strains of *B. longum* and *Eubacterium rectale*. Targeting of specific acetate and butyrate genes through gene prediction from 16S sequence data confirmed that acetate kinase was present at higher abundance in the in vitro system compared to butyrate kinase and acetyl-CoA transferase, and the same trend was observed in the XOS fermentations compared to the no-prebiotic controls. In addition, butyrate producers belonging to the Lachnospiraceae and Ruminococcaceae family, including Ruminococcus, *Coprococcus* and *Oscillospira*, were also present in higher abundance in the no-prebiotic controls. This suggests the possibility that butyrate producers may have been washed out during successive transfers. A similar finding was also observed in an in vitro fermentation model using infant stool samples. However, under in vivo conditions, the high acetate levels produced by CR15 would be expected to cross-feed butyrate producers, increase butyrate levels, and provide health benefits to the host.

In the latter study, supplementation of infant fecal fermentations with GOS exerted a bifidogenic effect with high concentrations of acetate, low concentrations of butyrate and low fecal pH. Interestingly, pH has previously been reported to influence bacteria communities and production of SCFA in vitro. This implies that improved buffering or pH control should be considered when designing batch in vitro models to study fecal communities and their metabolic byproducts.

Prebiotics are defined, in part, by virtue of their utilization by host microbes. Although functional demonstration of the specific mechanisms by which XOS transport and utilization occurs in bifidobacteria has not yet been established, two models have been proposed. In one model, extracellular xylolytic enzymes degrade XOS, and then xylose monomers are transported into the cell. Alternatively, XOS are transported via an ABC transport system, and intracellular XOS is hydrolyzed. The resulting xylose monomers are phosphorylated to form xylulose-5-P which then enters the *Bifidobacterium* shunt. Gene clusters encoding for putative glycosyl hydrolases have been identified, including GH8, GH43 and GH120. These clusters include genes encoding for non-reducing end β-xylosidase, reducing-end xylose-releasing exo-oligoxylanase and endo-1,4-β-xylanase, each having a preferred oligomer length. Based on the current genome annotations, the presence of GH43 and GH120 clusters and genes encoding for ABC-type permeases in *B. longum* subsp. *longum* CR15 suggest that the strain was capable of intracellular degradation of XOS.

Like other in vitro models, limitations exist with the IVE method. However, despite these limitations, the IVE model serves as a useful tool to identify potential synergistic pairs and then for testing those pairings across multiple samples. Such in vitro methodologies can accelerate the process of strain discovery and synbiotic pairing prior to in vivo trials to validate these formulations. Finally, more sophisticated and controlled in vitro models would provide a basis for greater throughput and increase the library of strains that can be collected in a short amount of time.

Other attempts to identify synbiotic combinations have generally relied on pairing previously isolated probiotic strains with one or more prebiotics. Indeed, these and many of the other synbiotic combinations described in the literature would be considered as complementary. While these approaches have the advantage of having characterized strains as the probiotic component, there is no a priori reason why the prebiotic would necessarily support growth of the probiotic in vivo. Accordingly, the enrichment method described in this study provides a basis for identifying putative probiotic strains that would be predicted to out-compete other resident microbes for the prebiotic. Provided these probiotic-prebiotic combinations result in a health benefit to the host, they would satisfy the definition of a synergistic synbiotic.

SEQUENCE LISTING

The patent contains a lengthy sequence listing. A copy of the sequence listing is available in electronic form from the USPTO web site (https://seqdata.uspto.gov/?pageRequest=docDetail&DocID=US11752178B2). An electronic copy of the sequence listing will also be available from the USPTO upon request and payment of the fee set forth in 37 CFR 1.19(b)(3).

What is claimed is:

1. A synbiotic composition comprising:
a probiotic species selected from the group consisting of *B. pseudocatenulatum*, *B. longum* subsp. *longum*, and any combination thereof, wherein the *B. longum* subsp. *longum* has a nucleotide sequence having at least 99% sequence identity to SEQ ID NO. 5; and
a prebiotic comprising an amount of xylooligosaccharide.

2. The synbiotic composition of claim 1, wherein the probiotic species is *B. longum* subsp. *longum*.

3. The synbiotic composition of claim 1, further comprising at least one enzyme.

4. The synbiotic composition of claim 1, wherein the composition is in a form selected from the group consisting of liquids, solids, tablets, pills, capsules, solids in a liquid medium, powders, lozenges, straws, sachets, cachets, solutions, elixirs, suspensions, emulsions, solutions, syrups, aerosols, gelatin capsules, sterile packaged powders, or combined with or introduced into a food product.

5. The synbiotic composition of claim 1, wherein the prebiotic further comprises at least one component selected from the group consisting of soluble starch, yeast extract, oligosaccharides, polysaccharides, and other prebiotics that contain fructose, xylose, soya, galactose, glucose and/or mannose.

6. The synbiotic composition of claim 1, wherein the prebiotic further comprises at least one component selected from the group consisting of polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

7. The synbiotic composition of claim 1, further comprising one or more additional active ingredients, excipients, dissolution agents, surfactants, antioxidants, antiseptics, preservatives, penetrants, osmoprotectants, cryoprotectants, and combinations thereof.

8. The synbiotic composition of claim 1, wherein the probiotic is lyophilized.

9. The synbiotic composition of claim 1, wherein said *B. longum* subsp. *longum* probiotic or *B. pseudocatenulatum* probiotic has a nucleotide sequence that includes at least 50 contiguous nucleotides having at least 95% sequence identity with a contiguous nucleotide sequence selected from the group consisting of SEQ ID NOs 5 or 6 or any one of SEQ ID NOs 15-99.

10. A method of improving gut health comprising a step of orally administering a therapeutically effective amount of the composition of claim 1 to a subject in need thereof.

11. The method of claim 10, wherein improving gut health is determined by assessing a gastrointestinal characteristic or parameter.

12. The method of claim 10, wherein the prebiotic and probiotic are administered within 6 hours of one another.

13. The method of claim 10, wherein gut health is improved by at least 10% in comparison to a subject or group of subjects that has not had an administration of the composition of claim 1 or is in comparison to the same subject before and after administration of the composition of claim 1.

14. The method of claim 10, wherein the composition is administered in a form selected from the group consisting of liquids, solids, tablets, pills, capsules, solids in a liquid medium, powders, lozenges, straws, sachets, cachets, solutions, elixirs, suspensions, emulsions, solutions, syrups, aerosols, gelatin capsules, sterile packaged powders, or combined with or introduced into a food product.

15. A method of modulating gastrointestinal microbiota in a subject comprising a steps of orally administering a therapeutically effective amount of the composition of claim 1 to a subject in need thereof.

16. The method of claim 15, wherein modulating gastrointestinal microbiota is determined by comparing the microbiota populations in the subject before and after administration of the composition of claim 1.

17. A method of increasing butyrate levels in the gut comprising a step of orally administering the composition of claim 1 to a subject in need thereof.

* * * * *